United States Patent
Golzarian et al.

(10) Patent No.: US 10,179,187 B2
(45) Date of Patent: *Jan. 15, 2019

(54) BIORESORBABLE EMBOLIZATION MICROSPHERES

(71) Applicant: Regents of the University of Minnesota, St. Paul, MN (US)

(72) Inventors: Jafar Golzarian, Plymouth, MN (US); Lihui Weng, Woodbury, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 1012 days.

This patent is subject to a terminal disclaimer.

(21) Appl. No.: 14/098,443

(22) Filed: Dec. 5, 2013

(65) Prior Publication Data
US 2014/0099374 A1 Apr. 10, 2014

Related U.S. Application Data

(63) Continuation of application No. 12/899,238, filed on Oct. 6, 2010, now Pat. No. 8,617,132.
(Continued)

(51) Int. Cl.
| | | |
|---|---|---|
| *A61B 19/00* | (2006.01) | |
| *A61L 24/08* | (2006.01) | |
| *A61L 24/00* | (2006.01) | |

(52) U.S. Cl.
CPC ........... *A61L 24/08* (2013.01); *A61L 24/0015* (2013.01); *A61L 2300/406* (2013.01);
(Continued)

(58) Field of Classification Search
CPC ................................. A61L 31/10; A61L 24/08
See application file for complete search history.

(56) References Cited

U.S. PATENT DOCUMENTS 4,758,223 A * 7/1988 Rydell .............. A61M 25/1018
604/191
5,514,379 A * 5/1996 Weissleder ........... A61K 9/1658
424/426
(Continued)

FOREIGN PATENT DOCUMENTS

CN 1481907 A * 3/2004 .......... A61L 31/041
CN 1762332 A 4/2006
(Continued)

OTHER PUBLICATIONS

Liu YF, et al. Preparation and characterization of glutaraldehyde cross-linked O-carboxymethylchitosan microspheres for controlled delivery of pazufloxacin mesilate. Int J Biol Macromol. Jun. 1, 2007;41(1)L87-93.*
(Continued)

*Primary Examiner* — Laura A Bouchelle
(74) *Attorney, Agent, or Firm* — Shumaker & Sieffert, P.A.

(57) ABSTRACT

The present disclosure is generally directed to an embolic material which, in some embodiments, may be in the form of a microsphere or a plurality of microspheres. The embolic material generally comprises carboxymethyl chitosan (CCN) crosslinked with carboxymethyl cellulose (CMC). In some embodiments, the embolic material may further comprise a therapeutic agent, such as doxorubicin.

32 Claims, 37 Drawing Sheets

Related U.S. Application Data

(60) Provisional application No. 61/249,194, filed on Oct. 6, 2009.

(52) U.S. Cl.
CPC ..... *A61L 2300/622* (2013.01); *A61L 2430/36* (2013.01); *Y10T 428/2982* (2015.01)

(56) References Cited

U.S. PATENT DOCUMENTS

| | | | |
|---|---|---|---|
| 5,635,215 A | | 6/1997 | Boschetti et al. |
| 5,648,100 A | | 7/1997 | Boschetti et al. |
| 6,197,346 B1 | | 3/2001 | Mathiowitz et al. |
| 6,960,617 B2 | * | 11/2005 | Omidian ............... A61K 9/0065 521/102 |
| 7,407,646 B2 | | 8/2008 | Laurent et al. |
| 8,617,132 B2 | | 12/2013 | Golzarian et al. |
| 8,741,351 B2 | | 6/2014 | Vogel et al. |
| 8,936,795 B2 | | 1/2015 | Golzarian et al. |
| 2002/0012705 A1 | * | 1/2002 | Domb ................... A61K 9/1652 424/493 |
| 2004/0071776 A1 | | 4/2004 | Boudy et al. |
| 2005/0263916 A1 | | 12/2005 | Lanphere et al. |
| 2006/0067883 A1 | | 3/2006 | Krom et al. |
| 2006/0105014 A1 | | 5/2006 | Cruise |
| 2006/0165804 A1 | * | 7/2006 | Lewis ................... A61K 9/1641 424/489 |
| 2006/0199010 A1 | | 9/2006 | DiCarlo et al. |
| 2006/0210635 A1 | | 9/2006 | Laurent et al. |
| 2007/0014831 A1 | * | 1/2007 | Sung ................ A61B 17/12022 424/426 |
| 2007/0031467 A1 | * | 2/2007 | Abrahams ............ A61L 24/043 424/423 |
| 2007/0148768 A1 | * | 6/2007 | Liao ..................... C12N 5/0068 435/325 |
| 2007/0264310 A1 | * | 11/2007 | Hissong ................ A61F 11/002 424/437 |
| 2008/0039890 A1 | | 2/2008 | Matson et al. |
| 2008/0041715 A1 | | 2/2008 | Lanphere et al. |
| 2009/0117196 A1 | | 5/2009 | Boschetti |
| 2011/0082427 A1 | | 4/2011 | Golzarian et al. |
| 2011/0142965 A1 | | 6/2011 | Walke |
| 2013/0330292 A1 | | 12/2013 | Lei et al. |
| 2014/0099374 A1 | | 4/2014 | Golzarian et al. |
| 2014/0171907 A1 | | 6/2014 | Golzarian et al. |
| 2014/0274945 A1 | | 9/2014 | Blaskovich et al. |
| 2014/0274954 A1 | | 9/2014 | Chellappan et al. |
| 2017/0273888 A1 | | 9/2017 | Weng et al. |

FOREIGN PATENT DOCUMENTS

| | | |
|---|---|---|
| CN | 1939316 A | 4/2007 |
| CN | 101125225 A | 2/2008 |
| CN | 101209354 A | 7/2008 |
| EP | 1508344 A1 | 2/2005 |
| EP | 1810698 A1 | 7/2007 |
| EP | 2626088 A1 | 8/2013 |
| EP | 2803370 A1 | 11/2014 |
| WO | 2009056602 A1 | 5/2009 |
| WO | 2009072146 A1 | 6/2009 |
| WO | 2011044236 A1 | 4/2011 |
| WO | 2014152488 A2 | 9/2014 |
| WO | 2015033093 A1 | 3/2015 |

OTHER PUBLICATIONS

Second Office Action, and partial translation thereof, from counterpart Chinese Application No. 201410471833.6, dated May 19, 2016, 12 pp.
Office Action, and translation thereof, from counterpart Korean Application No. 10-2013-7034806, dated Oct. 7, 2015, 7 pp.
First Office Action, and partial translation thereof, from counterpart Chinese Application No. 201410471833.6, dated Sep. 22, 2015, 14 pp.
Response to Communication dated Nov. 24, 2014, from counterpart European Patent Application No. 14180732.1, filed May 6, 2015, 7 pp.
Search Report from Counterpart European Patent Application No. 14180732.1, dated Oct. 22, 2014, 7 pp.
Notice of Allowance from U.S. Appl. No. 13/720,135, dated Sep. 4, 2014, 8 pp.
Advisory Action from U.S. Appl. No. 13/720,135, dated May 29, 2014, 4 pp.
Pre-Appeal Brief Request for Review for U.S. Appl. No. 13/720,135, dated Jun. 19, 2014, 5 pp.
Response to Final Office Action from co-pending U.S. Appl. No. 13/720,135, filed Apr. 21, 2014, 10 pp.
Examination Report issued in the corresponding Australian patent application No. 2013204366 dated Feb. 27, 2014. 2 pp.
Final Office Action from the corresponding U.S. Appl. No. 13/720,135, dated Feb. 19, 2014. 11 pp.
Written Opinion and Search Report from corresponding PCT Application No. PCT/US2010/051629, dated Feb. 23, 2011 (11 pp).
Kettenbach et al. "Drug-Loaded Microspheres for the Treatment of Liver Cancer: Review of Current Results", Cardiovasc Intervent Radiol (Jan. 29, 2008) 31:468-476 (9 pp).
International Preliminary Report on Patentablity from corresponding PCT Application No. PCT/US2010/051629, dated Apr. 19, 2012, 6 pages.
Laurent, "Microspheres and Nonspherical Particles for Embolization," Techniques in Vascular and Interventional Radiology, vol. 10, No. 4, Dec. 1, 2007, 10 pages.
Ohta et al., "Degradable Gelatin Microspheres as an Embolic Agent: An Experimental Study in a Rabbit Renal Model," Korean J. Radiol 8(5), Oct. 2007, pp. 418-428.
Nitta et al., "Gelatin Microspheres: Initial Clinical Experience for the Transcatheter Arterial Embolization," European Journal of Radiology, vol. 67, Issue 3, Sep. 2008, 536-540.
Wang et al., "Preparation and Characterization of Pingyangmycin-loaded Bovine Serum Albumin Microspheres for Embolization Therapy," International Journal of Pharmaceutics, vol. 336, No. 2, May 24, 2007, pp. 361-366.
Laccourreye et al., "Biodegradable Starch Microspheres for Cerebral Arterial Embolization," Journal of Clinical and Laboratory Research, vol. 28, No. 2, Feb. 1993, pp. 150-154.
Flandroy et al., "(D,L) Polylactide Microspheres as Embolic Agent," Neuroradiology, vol. 32, No. 4, Feb. 1990, pp. 311-315.
Wu et al., "Preparation and Drug Release Characteristics of Pingyangmycin-Loaded Dextran Cross-Linked Gelatin Microspheres for Embolizalion Therapy," Journal of Biomedical Materials Research, Part B, vol. 78B, Issue I, Jul, 2006, 56-62
Liu et al., "A Study of Doxorubicin Loading Onto and Release from Sulfopropyl Dextran Ion-Exchange Microspheres," Journal of Controlled Release, vol. 77, Dec. 2001, pp. 213-224.
European Search Report from Application No. 13160331.8, dated Jul. 16, 2013, 4 pages.
Office Action from corresponding Korean patent application No. 10-2012-7011638, dated Aug. 7, 2013, 7 pp.
Office Action dated Jul. 22, 2013 for U.S. Appl. No. 13/720,135 (11 pgs.).
Responsive amendment, dated Oct. 22, 2013, for U.S. Appl. No. 13/720,135, 11 pages.
First Examination Report from counterpart Australian Application No. 2015202025, dated Sep. 18, 2015, 2 pp.
Grosso et al., Transarterial Chemoembolization for Hepatocellular Carcinoma with Drug-Eluting Microspheres: Preliminary Results from an Italian Multicentre Study, Cardiovascular Interventional Radiology, vol. 31(6), Aug. 12, 2008, pp. 1141-1149.
Haijun et al., "Effects of Carboxymethylchitosan-carboxymethylcellulose Membrane on Extraneural Adhesion Formation and Peripheral Nerve Regeneration," Journal of Clinical Rehabilitative Tissue Engineering Research, vol. 13(34), Aug. 20, 2009, 5 pp. (English Translation of Abstract Only.).
English Translation of Chinese Office Action from Chinese counterpart application No. 201080055018.1, dated Jan. 23, 2014, 3 pp.

(56) References Cited

OTHER PUBLICATIONS

The Notification of Rejection, and partial translation thereof, from counterpart Chinese Application No. 201410471833.6, dated Sep. 12, 2016, 15 pp.
Barnett et al., "In Vitro Assessment of EmboGel and UltraGel Radiopaque Hydrogels for the Endovascular Treatment of Aneurysms," Journal of Vascular Interventional Radiology, Apr. 2009, 20:507-512.
Brennecka et al., "In Vivo Experimental Aneurysm Embolization in a Swine Model with a Liquid-to-Solid Gelling polymer System: Initial Biocompatibility and Delivery Strategy Analysis," World Neurosurgery, Nov. 2012; 78(5):469-80 (Epublished Nov. 1, 2011).
Fatimi et al., "A New Injectable Radiopaque Chitosan-Based Sclerosing Embolizing Hydrogel for Endovascular Therapies," Acta Biomaterialia, Jul. 2012; 8(7):2712-21 (Epublished Apr. 2012).
International Campaign Against Microbeads in Cosmetics, accessed from www.beatthemicrobead.org on Jul. 2015, 4 pp.
Kazekawa et al., "Newly Synthesized Liquid Embolization Material for Arteriovenous Malformation," Journal Clinical Neuroscience, Mar. 1998, 45-48 pp.
Ko et al., "Preoperative Portal Vein Embolization with a New Liquid Embolic Agent," Radiology, May 2003, vol. 227, Vo. 2, 407-413 (Epublished Mar. 13, 2003).
Kutlu et al, "Pulmonary Embolism After Penile Deep Dorsal Vein Embolization with n-butyl-2-cyanoacrylate and Lipiodol Mixture" European Journal Radiology Extra, Mar. 2004, 49(3), 103-106 pp.
Mottu et al., "Iodine-Containing Cellulose Mixed Esters as Radiopaque Polymers for Direct Emoblization of Cerebral Aneurysms and Arteriovenous Malformations," Biomaterials, Jan. 2002, 23(1), 121-131 pp.
Pollak et al., "The Use of Cyanoacrylate Adhesives in Peripheral Embolization," Journal of Vascular Interventional Radiology, Aug. 2001,12, 907-913 pp.
Shi et al., "Therapeutic Embolization of Meningiomas with Onyx for Delayed Surgical Resection," Surgical Neurology, Nov. 2008, 70:478-481 (Epublished Feb. 8, 2008).
Silas et al., "Sclerosis of Postoperative Lymphoceles: Avoidance of Prolonged Catheter Drainage with Use of a Fibrin Sealant," Journal of Vascular Interventional Radiology, Nov. 2006, 17:1791-1795.
Su et al., "Histopathological Studies of a New Liquid Embolization Method Using Estrogen-Alcohol and Polyvinyl Acetate: Experimental Evaluations with a Model of Cortical Arterial Cannulation in the Canine Brain," Surgical Neurology, Jul. 1991, vol. 36, No. 1, 4-11 pp.
Weng et al., "Bioresorbable Hydrogel Microspheres for Transcatheter Embolization: Preparation and in Vitro Evaluation," Laboratory Investigation, Jun. 15, 2011, 9 pp.
Weng et al., "Calibrated Bioresorbable Microspheres as an Embolic Agent: An Experimental Study in a Rabbit Renal Model," HHS Public Access, PMC Oct. 4, 2016, 15 pp.
Weng et al., "Doxorubicin loading and eluting characteristics of bioresorbable hydrogel microspheres: in vitro study," International Journal of Pharmaceutics, vol. 409, Issues 1-2, May 16, 2011, 185-193 pp.
Weng et al., "In vitro and in vivo evaluation of biodegradable embolic microspheres with tunable anticancer drug release," Acta Biomaterialia, Elsevier, vol. 9, Issue 6, Jun. 2013, 12 pp.
Weng et al., "In Vitro Assessment of an in Situ Gelable Hydrogel for Adjunct Endovascular Treatment of Abdominal Aortic Aneurysms," Journal of Vascular and Interventional Radiology, Abstract 346, Mar. 2012, 23(3): S139.
Kim et al., "MRI Visible Drug Eluting Magnetic Microspheres for Transcatheter Intra-Arterial Delivery to Liver Tumors," Theranostics, vol. 5, Issue 5, Feb. 7, 2015, 12 pp.
Kim et al., "Multimodal Imaging of Nanocomposite Microspheres for Transcatheter Intra-Arterial Drug Delivery to Liver Tumors," Scientific Reports, Jul. 13, 2016, 10 pp.
Sommer et al., "Multimodal Visibility (Radiography, Computed Tomography, and Magnetic Resonance Imaging) of Microspheres for Transarterial Embolization Tested in Porcine Kidneys," Investigative Radiology, vol. 48, No. 4, Apr. 2013, 10 pp.
Weng et al., "Synthesis and in vitro evaluation of MRI visible resorable and loadable microspheres for arterial embolization," Abstract only submitted for the SIR Annual Scientific Meeting, downloaded Jan. 25, 2018, 2 pp.
Examination Report from counterpart European Application No. 14180732.1, dated Apr. 4, 2018, 4 pp.
Response to Extended Search Report dated Apr. 4, 2018, from counterpart European Application No. 14180732.1, filed Jul. 17, 2018, 10 pp.
Notice of Intent to Grant and Text Intended to Grant from counterpart European Application No. 14180732.1, dated Sep. 21, 2018, 85 pp.

* cited by examiner

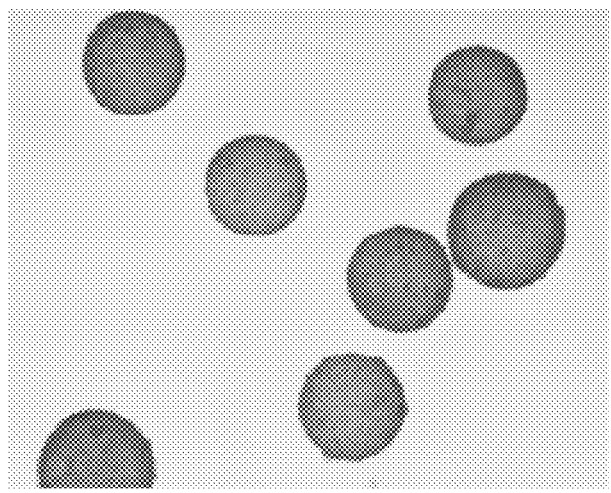
FIG. 6A
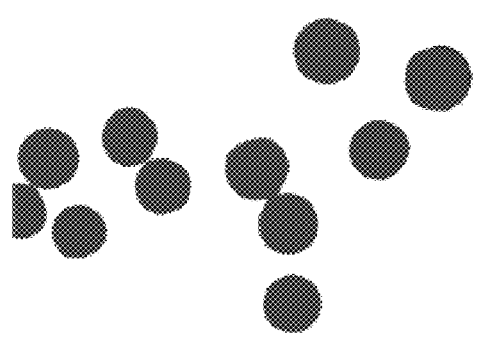    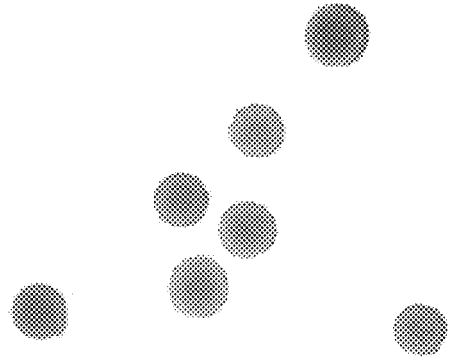
FIG. 6B            FIG. 6C

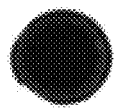 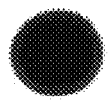
FIG. 27A　　　　　　　　FIG. 27B
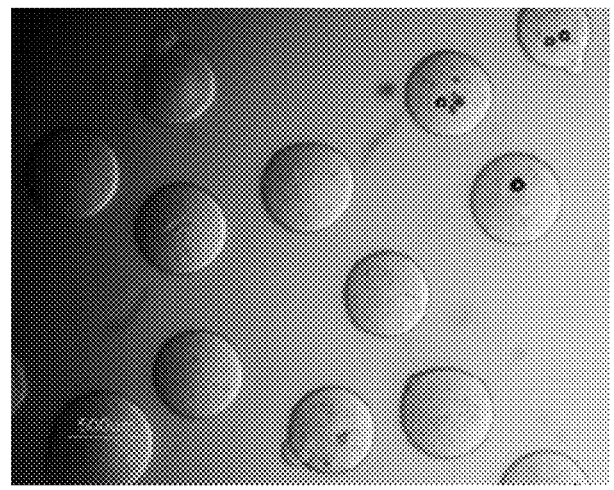
FIG. 28

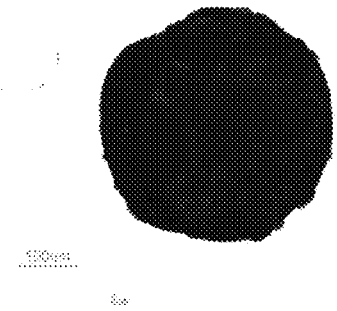
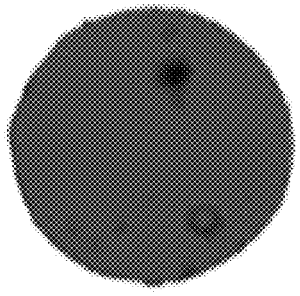
FIG. 35A  FIG. 35B
FIG. 35C

BIORESORBABLE EMBOLIZATION MICROSPHERES

This application is a continuation of U.S. application Ser. No. 12/899,238, entitled "BIORESORBABLE EMBOLIZATION MICROSPHERES," filed Oct. 6, 2010, which claims the benefit of U.S. Provisional Application No. 61/249,194, entitled, "EMBOLIZATION MICROSPHERES," filed on Oct. 6, 2009, the entire contents of which are incorporated herein by reference.

TECHNICAL FIELD

The disclosure relates to embolic materials.

BACKGROUND

Transcatheter arterial embolization (TAE) has been widely accepted for its efficacy in treating various diseases including tumors, vascular lesions, and hemorrhages. For a safe and effective treatment, the selection of an appropriate embolic material is important.

SUMMARY

In general, the disclosure is directed to an embolic material comprising carboxymethyl chitosan (CCN) crosslinked with carboxymethyl cellulose (CMC). The embolic material may be formed into microspheres with a diameter between about 50 micrometers (μm) and about 2200 μm. CCN and CMC each are biodegradable and biocompatible. In preparing the embolic material, CCN may be crosslinked by partially oxidized CMC, without use of a small molecule crosslinking agent. Because of this, the embolic material is expected to be biodegradable and biocompatible. Additionally, because the embolic material comprises a three-dimensional network of CCN crosslinked by CMC, the mechanical properties, such as, for example, the compressibility of the embolic microspheres, may be sufficient to permit introduction of the microspheres into an artery of a patient through a syringe, catheter, or the like.

In some embodiments, the embolic microspheres may additionally comprise a therapeutic agent, such as an anticancer agent. One example of a therapeutic agent which may be loaded into the embolic microspheres is doxorubicin.

In one aspect, the disclosure is directed to an embolic material comprising a microsphere having a diameter between about 50 μm and about 2200 μm, where the microsphere comprises carboxymethyl chitosan crosslinked with carboxymethyl cellulose.

In another aspect, the disclosure is directed to an embolization suspension comprising a solvent and a plurality of microspheres suspended in the solvent. According to this aspect of the disclosure, at least one of the plurality of microspheres comprises a diameter between about 50 μm and about 2200 μm, and at least one of the plurality of microspheres comprises carboxymethyl chitosan crosslinked with carboxymethyl cellulose.

In a further aspect, the disclosure is directed to a kit comprising a plurality of microspheres, where at least one of the plurality of microspheres comprises a diameter between about 50 μm and about 2200 μm, and where at least one of the plurality of microspheres comprises carboxymethyl chitosan crosslinked with carboxymethyl cellulose. According to this aspect of the disclosure, the kit further comprises a syringe or vial in which the plurality of microspheres is disposed.

In an additional aspect, the disclosure is directed to a method of forming an embolic microsphere. The method comprises at least partially oxidizing carboxymethyl cellulose (CMC) to form partially oxidized CMC; forming an emulsion of partially oxidized CMC, carboxymethyl chitosan (CCN), water, and an oil; and crosslinking the CCN with the CMC to form the embolic microsphere.

In a further aspect, the disclosure is directed to a method comprising injecting an embolic microsphere comprising carboxymethyl chitosan crosslinked with carboxymethyl cellulose in a blood vessel of a patient to occlude an artery of the patient.

The details of one or more embodiments are set forth in the accompanying drawings and the description below. Other features, objects, and advantages of the disclosure will be apparent from the description and drawings, and from the claims.

BRIEF DESCRIPTION OF DRAWINGS

FIGS. 6A-6C illustrate examples of microspheres according to an aspect of the disclosure after being loaded with various dyes.

FIGS. 27A and 27B illustrate an example of the resiliency of a microsphere comprising CCN crosslinked with CMC (dyed with Evan's blue).

FIG. 28 is a light microscopy image of an example of microspheres comprising CCN crosslinked with CMC and having diameters between about 500 μm and about 700 μm after being injected through a catheter with an internal diameter of about 667 μm (2 French).

FIGS. 35A-35C are light microscopy images that illustrate an example of a plurality of microspheres loaded with doxorubicin degrading in the presence of lysozyme.

DETAILED DESCRIPTION

The present disclosure is generally directed to an embolic material which, in some embodiments, may be in the form of a microsphere or a plurality of microspheres. The embolic material generally comprises carboxymethyl chitosan (CCN) crosslinked with carboxymethyl cellulose (CMC).

Temporary embolization may be accomplished by a material that is spherical, biocompatible, bioresorbable, and compressible. However, these properties are not easily achieved in a single embolic microsphere. For example, crosslinking of polymers may be accomplished by using a small molecule crosslinking agent, such as glutaraldehyde. While use of the small molecule crosslinking agent facilitates the desired crosslinking reaction, if the crosslinked polymer is biodegradable and degrades in a body of a patient, some small-molecule crosslinking agents may be toxic or have other adverse effects on cells or tissue in the body of the patient.

In accordance with aspects of this disclosure, CCN and CMC may be crosslinked without use of a small molecule crosslinking agent to form embolic microspheres that are substantially free of small molecule crosslinking agent. In fact, in some embodiments, the crosslinking reaction between CMC and CCN may be carried out without a small molecule crosslinking agent and at relatively low temperatures (e.g., about 50° C.) in a water and oil emulsion. CCN is substantially non-toxic and biodegradable. Chitosan breaks down in the body to glucosamine, which can be substantially completely absorbed by a patient's body. Similarly, CMC is substantially non-toxic and biodegradable. Thus a crosslinked polymer formed by CCN and CMC is expected to the substantially non-toxic (i.e., biocompatible) and biodegradable (or bioresorbable). Additionally, because the crosslinked CCN and CMC microsphere is formed from two polymers, the mechanical properties, such as compressibility, of the crosslinked molecule are expected to be sufficient for injection of the crosslinked molecule through a syringe or catheter.

Because the crosslinking reaction between CCN and CMC may be performed at a relatively low temperature, the crosslinking reaction may be relatively slow in some examples. For example, the crosslinking reaction may be carried out over night (e.g., over at least about 12 hours). Such a reaction may result in roughly spherical crosslinked particles (microspheres). In some examples, an average diameter of the microspheres may be between about 50 μm and about 2200 μm, depending on reaction conditions (e.g., stirring speed, initial concentrations of reactants, time, temperature, or the like).

Figure 1:
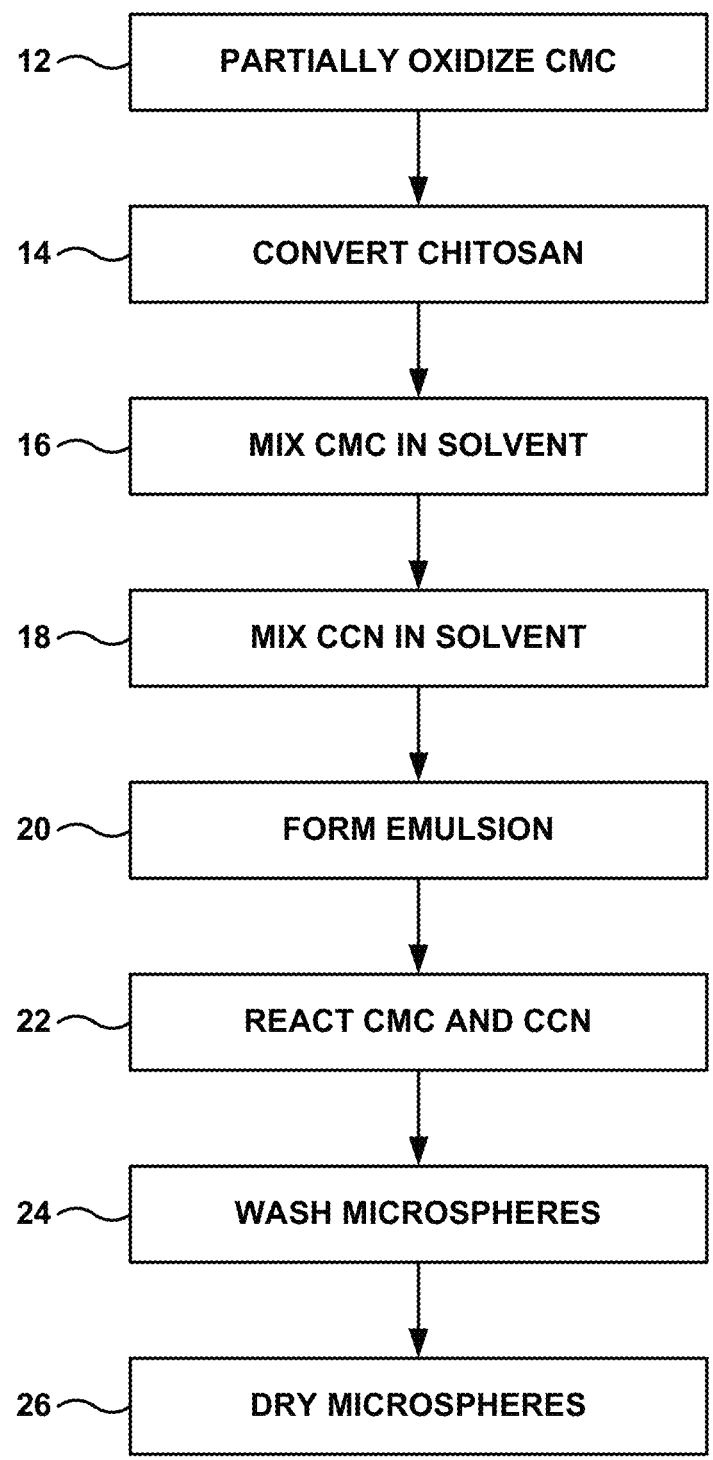
FIG. 1 is a flow diagram of an example technique for producing embolic microspheres comprising carboxymethyl chitosan crosslinked with carboxymethyl cellulose.

In some embodiments, the microspheres comprising CCN and CMC may be formed according to the technique illustrated in FIG. 1. Initially, CMC is at least partially oxidized to form partially oxidized CMC (12). One reaction that at least partially oxidizes CMC is illustrated in Reaction 1:

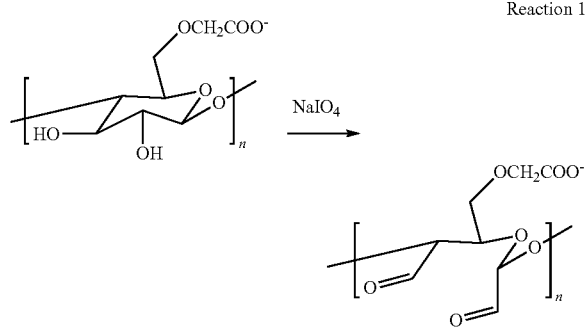

Reaction 1

In Reaction 1, a single CMC monomer (repeating unit), which is part of a chain comprising n repeating units, is reacted with $NaIO_4$ (sodium periodate) at about 25° C. to oxidize the C—C bond between carbon atoms bonded to hydroxyl groups to form carbonyl (more particularly aldehyde) groups. Reaction 1 shows only a single repeating unit of the CMC polymer. In some embodiments, not all repeating units within the CMC polymer may be oxidized. For example, some repeating units may not be oxidized at all, and may still include two hydroxyl groups after Reaction 1 is performed. Other monomers may be oxidized, and may include two carbonyl groups, as illustrated in Reaction 1. The CMC may include a weight average molecular weight of between about 50,000 daltons (Da; equivalent to grams per mole (g/mol)) and about 800,000 Da. In some embodiments, a weight average molecular weight of the CMC may be about 700,000 g/mol.

The degree of oxidation of the CMC may be affected by, for example, the molar ratio of $NaIO_4$ to CMC repeating units. In some embodiments, the molar ratio of $NaIO_4$ molecules to CMC repeating units may be between about 0.1:1 and about 0.5:1 ($NaIO_4$:CMC). Particular examples of molar ratios of $NaIO_4$ molecules to CMC repeating units include about 0.1:1, about 0.25:1, and about 0.5:1. An increased molar ratio of $NaIO_4$ molecules to CMC repeating units may result in greater oxidation of the CMC, which in turn may lead to greater crosslinking density when CMC is reacted with CCN to form the embolic microspheres. Conversely, a decreased molar ratio of $NaIO_4$ molecules to CMC repeating units may result in lesser oxidation of the CMC, which in turn may lead to lower crosslinking density when CMC is reacted with CCN to form the embolic microspheres. In some examples, the crosslinking density may be approximately proportional to the degree of oxidation of the CMC. In some embodiments, a greater crosslinking density may lead to greater mechanical strength (e.g., fracture strain).

CCN may then be prepared by reacting chitosan to attach —$CH_2COO^-$ groups in place of one of the hydrogen atoms in an amine group or a hydroxyl group, as illustrated in Reaction 2 (14).

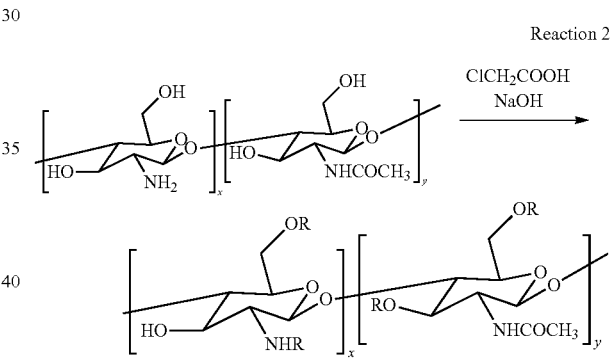

Reaction 2

In the product of Reaction 2, each R is independently either H or —$CH_2COO^-$. Similar to oxidation of CMC shown in Reaction 1, the extent of the addition of the —$CH_2COO^-$ may affect the crosslink density when the CCN is reacted with the partially oxidized CMC to form the embolic microspheres. In some embodiments, the ratio of x:y may be about 3:1 (i.e., monomers of "x" form about 75% of the chitosan and monomers of "y" form about 25% of the chitosan). In some embodiments, the chitosan starting material may have a molecular weight between about 190,000 g/mol and about 375,000 g/mol. In some examples, Reaction 2 may be performed by stirring the reaction mixture at 500 rpm for about 24 hours at about 25° C., followed by stirring the reaction mixture at 500 rpm for about 4 hours at about 50° C.

Once the partially oxidized CMC and the CCN have been prepared, each is mixed in a respective amount of a solvent, such as water (16), (18). For example, 0.1 milligram (mg) of partially oxidized CMC may be mixed in 5 milliliter (mL) of water to form a first 2% weight/volume (w/v) solution. Similarly, 0.1 mg of CCN may be mixed in 5 mL of water to form a second 2% w/v solution. Of course, solvents other than water may be used, and solutions having other concentrations of partially oxidized CMC or CCN, respectively, may be utilized. For example, saline or phosphate-buffered saline (PBS) may be utilized as alternative solvents. The solvent used in the partially oxidized CMC solution may be the same as or different than the solvent used in the CCN solution. The solutions may have concentrations of partially oxidized CMC or CCN between about 0.5% w/v and about 3% w/v. The concentration of the partially oxidized CMC solution may be the same as or different from the concentration of the CCN solution.

The first and second solutions may then be added to another solvent to form an emulsion (20). In an example in which water is utilized as the solvent for the partially oxidized CMC and CCN, the other solvent may be an oil, such as, for example, mineral oil. In some embodiments, the other solvent may include mixed therein a surfactant. One example of a suitable surfactant includes sorbitan monooleate, available under the tradename S6760 or Span® 80 from Sigma-Aldrich, St. Louis, Mo. In one embodiment, 0.5 mL of sorbitan monooleate may be mixed in 50 mL of mineral oil, which is then mixed with the 5 mL 2% w/v solution of partially oxidized CMC and the 5 mL 2% w/v solution of CCN.

The emulsion is then left for at least about 12 hours (e.g., at least overnight) to allow the partially oxidized CMC and CCN to react (22) in a modified emulsion-crosslinking reaction. In particular, an amino group on the CCN may react with an aldehyde group on the partially oxidized CMC to form a Schiff base (i.e., an N═C double bond) and crosslink the CMC and the CCN. One such crosslinking reaction is shown below in Reaction 3.

the embolic microspheres are used. In this way, the microspheres formed from CCN crosslinked with CMC may be substantially free of any small-molecule crosslinking agent.

In some examples, the crosslinking reaction between CMC and CCN may proceed under relatively benign conditions. For example, the crosslinking reaction may be carried out at ambient pressures and ambient temperatures (e.g., room temperature). In some embodiments, the reaction may be carried out at a temperature above ambient, such as, for example, 50° C. Exemplary ranges of temperatures in which the crosslinking reaction may be performed include between about 20° C. and about 70° C., and at about 50° C. In some embodiments, a lower reaction temperature may necessitate a longer reaction time to result in substantially similar diameter microspheres, or may result in smaller microspheres after a similar amount of time.

One advantage of performing the reaction at a temperature above room temperature may be the removal of water from the reaction mixture during the course of the reaction. For example, performing the crosslinking reaction at a temperature of about 50° C. may result in evaporation of water as the crosslinking reaction proceeds.

An extent of crosslinking between molecules of CMC and CCN may affect mechanical properties of the resulting microsphere. For example, a greater crosslinking density generally may provide greater mechanical strength (e.g., fracture strain), while a lower crosslinking density may provide lower mechanical strength (e.g., fracture strain). In some embodiments, the crosslinking density may be adjustable to provide a fracture strain of between about 70% and Reaction 3

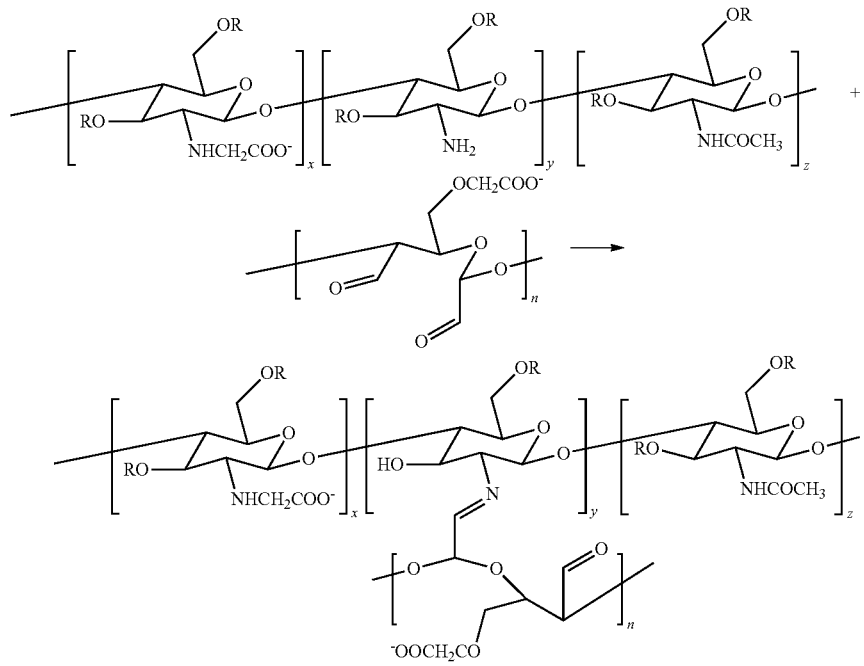

As discussed above, the crosslinking reaction of the CMC and CCN may proceed without use of a small-molecule crosslinking agent, such as glutaraldehyde. This may be advantageous, because in some embodiments, a small-molecule crosslinking agent may be toxic to a patient in which about 90%, as described below with respect to FIG. 24. The crosslinking density may also affect the degradation rate of the microsphere. For example, a greater crosslinking density may lead to a longer degradation time, while a lower crosslinking density may lead to a shorter degradation time.

In some examples, the crosslink bonds may degrade through hydrolyzing of the C=N double bond.

As described above, the crosslinking reaction between CMC and CCN is a modified emulsion-crosslinking reaction. In some examples, an emulsion-crosslinking reaction may be rate-limited by transport of the CMC and CCN molecules, and may play a role in the reaction product (the crosslinked CMC and CCN) being microspheres.

The size of the microspheres may be affected by reaction conditions, such as, for example, a stirring speed, a reaction temperature, a concentration of the CMC and CCN molecules in the reaction emulsion, an amount of mixing of the emulsion, or a concentration of the surfactant in the emulsion. For example, increasing the concentration of each of the CMC and CCN solutions from 1.5% w/v to 2% w/v while keeping the oxidation degree of CMC at about 25% (about 25 oxidized repeating units per 100 total repeating units), the stirring speed at 600 revolutions per minute (rpm), the temperature at about 50° C., the reaction time at about 12 hours, and the amount of Span 80 at about 0.3 mL/50 mL mineral oil, the average diameter of the microspheres may increase from about 600 µm to about 1100 µm. As another example, increasing the oxidation degree of CMC from about 10% to about 25% while keeping the concentration of each of the CMC and CCN solutions at about 1.5% w/v, the stirring speed at 600 rpm, the temperature at about 50° C., the reaction time at about 12 hours, and the amount of Span 80 at about 0.3 mL/50 mL mineral oil, the average diameter of the microspheres may increase from about 510 µm to about 600 µm.

In some embodiments, the reaction conditions may be selected to result in microspheres with a mean or median diameter between about 50 µm and about 2200 µm. In some embodiments, the reaction conditions may be selected to result in microspheres with a mean or median diameter of less than about 2000 µm, microspheres with a mean or median diameter of between about 100 µm and about 1200 µm, microspheres with a mean or median diameter of between about 100 µm and about 300 µm, microspheres with a mean or median diameter of between about 300 µm and about 500 µm, microspheres with a mean or median diameter of between about 500 µm and about 700 µm, microspheres with a mean or median diameter of between about 700 µm and about 900 µm, microspheres with a mean or median diameter of between about 900 µm and about 1200 µm, or microspheres with a mean or median diameter of between about 1600 µm and about 2000 µm.

In some examples, microspheres with different mean or median diameters may be used for different applications. For example, in some implementations, microspheres with a mean or median diameter between about 100 µm and about 300 µm may be loaded with a therapeutic agent, such as a chemotherapeutic agent as described further below, and used to deliver the therapeutic agent to a therapy site, while also embolizing blood vessels with a diameter similar to the mean or median diameter of the microspheres. In some embodiments, microspheres with a mean or median diameter between about 300 µm and about 500 µm may be used similarly, and loaded with a therapeutic agent. In some embodiments, microspheres with a larger mean or median diameter may be used as embolization materials, and may not be loaded with a therapeutic agent.

Once the reaction has proceeded for a desired amount of time to produce microspheres with a desired mean or median diameter, the water in the emulsion may be substantially fully removed, if the water has not already been evaporated during the crosslinking reaction. The microspheres may then be precipitated by a solvent, such as isopropanol. The oil phase may then be removed, such as by decanting or centrifugation, and the microspheres may be washed (24). For example, the microspheres may be washed with hexane and acetone. Finally, the microspheres may be dried (26) in air or under a vacuum.

In some embodiments, the crosslinking reaction may produce a plurality of microspheres with diameters distributed about a mean or median. In some cases, it may be advantageous to isolate microspheres with diameters within a smaller range or microspheres with substantially a single diameter. In some embodiments, the microspheres may be separated according to diameter by wet sieving in normal saline through a sieve or sieves with predetermined mesh size(s).

The microspheres may be packaged for distribution in various ways. For example, the microspheres may be distributed as part of a kit. In some embodiments, the kit may include the microspheres disposed in a syringe or a vial. The kit may optionally include a catheter, a guide wire, and/or a container of solution in which the microspheres are to be suspended. The catheter may be used to inject the microspheres into a blood vessel of a patient. The guide wire may be used to position the catheter within the blood vessel.

In some embodiments, the kit may be an emergency trauma kit for acute embolization in massive bleeding trauma. Such a kit may include, for example, a syringe or vial and a plurality of microspheres disposed in the syringe or vial. In some embodiments, the microspheres may comprise an average diameter of between about 1600 µm and about 2000 µm. In other embodiments, the microspheres may comprise a different average diameter, such as an average diameter within a range listed in other portions of this application. In some embodiments, the kit may further include a catheter, a guide wire for positioning the catheter within a blood vessel, such as an artery, of the patient, and/or a container of solution in which the microspheres are to be suspended. Prior to injection of the microspheres, the solution may be aspirated into the syringe to form a suspension of the microspheres in the solution.

The microspheres may be used to embolize arteries to treat various conditions, including, for example, an arteriovenous malformation, a cerebral aneurysm, gastrointestinal bleeding, an epistaxis, primary post-partum hemorrhage, or the like.

Figure 2A:
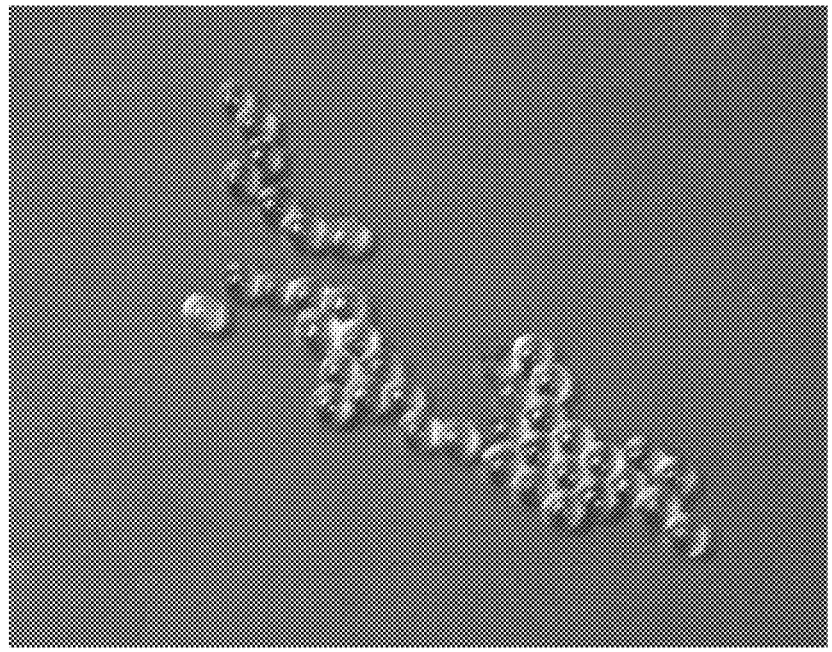
FIGS. 2A and 2B are a photograph and a light microscopy image, respectively, of microspheres in accordance with one aspect of the disclosure.
Figure 2B:
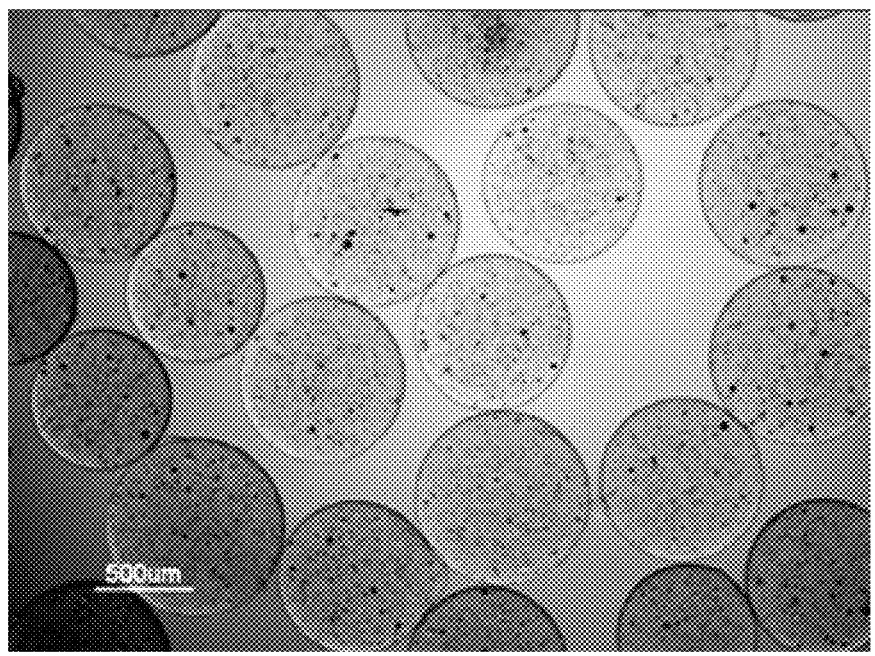

FIGS. 2A and 2B are a photograph and a light microscopy image of microspheres in accordance with one aspect of the disclosure. FIG. 2A illustrates that microspheres in accordance with the disclosure may be substantially spherical. FIG. 2B illustrates an example in which the diameter of the microspheres ranges from about 900 µm to about 1200 µm.

Figure 3:
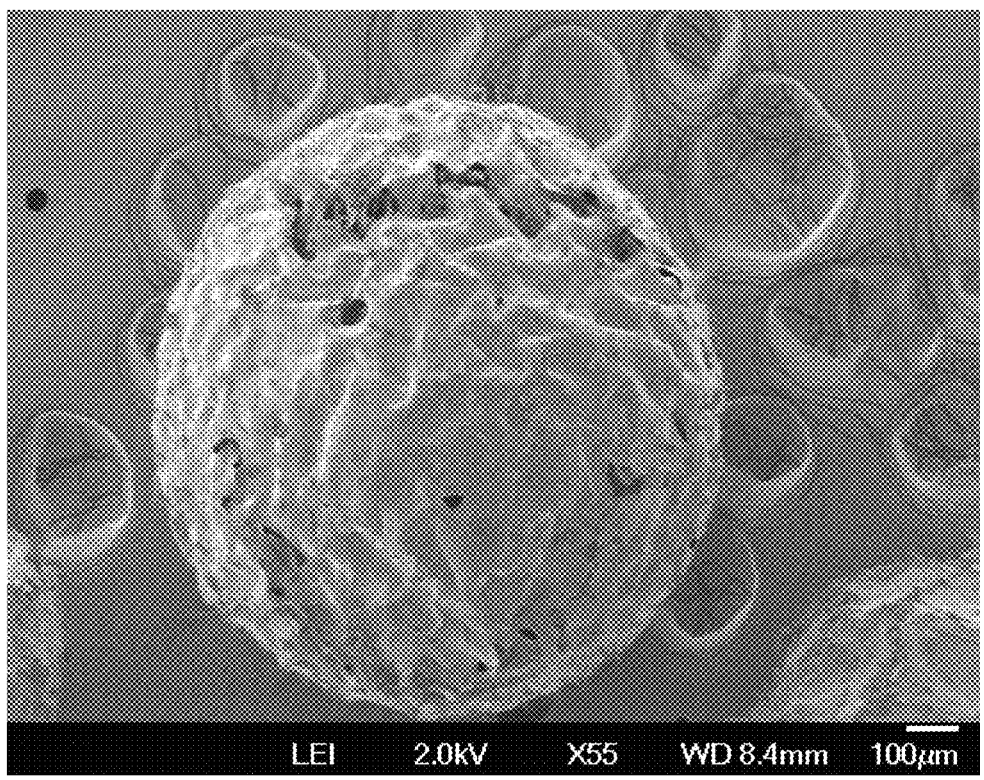
FIG. 3 is an example of a scanning electron microscopy image of an exterior of a microsphere formed in accordance with aspects of this disclosure.

FIG. 3 is an example scanning electron microscopy (SEM) image of an exterior of a microsphere formed in accordance with aspects of this disclosure. Prior to collection of the SEM image, the microsphere was lyophilized. Before lyophilization (freeze drying), saline was removed from the microsphere by rinsing the microsphere repeatedly with deionized water. The resulting microsphere was frozen in liquid nitrogen, and lyophilized to remove any residual water from pores of the microsphere. The SEM image was obtained utilizing a JEOL JSM-6700 SEM (available from JEOL USA, Inc., Peabody, Mass.). FIG. 3 was collected at 55× magnification at 2.0 kilovolts (kV). The microsphere in FIG. 3 had a diameter of about 1100 µm.

Figure 4A:
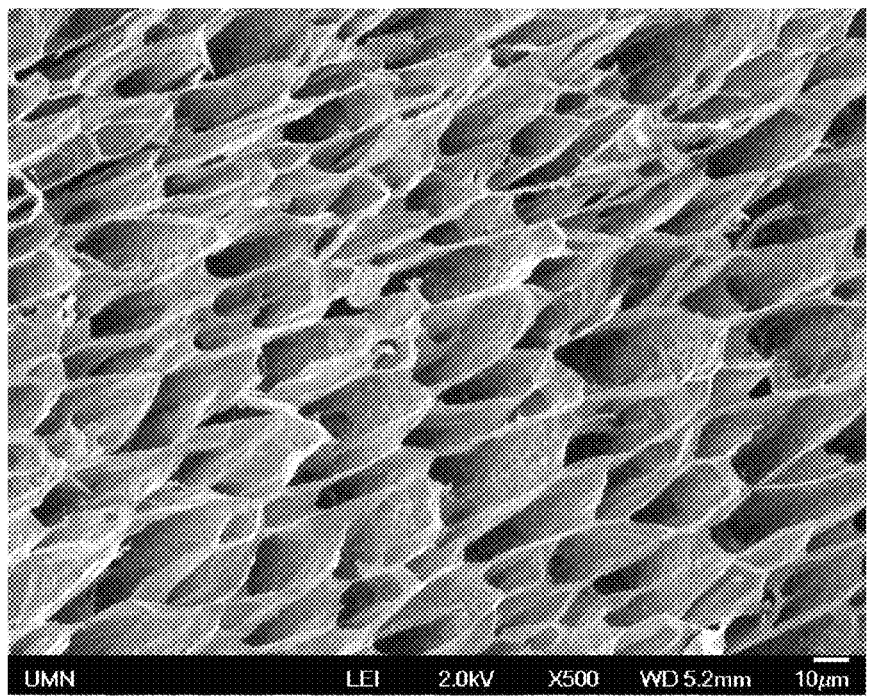
FIGS. 4A and 4B are examples of SEM images of the cross-section of a hydrogel prepared with CCN crosslinked with CMC.
Figure 4B:
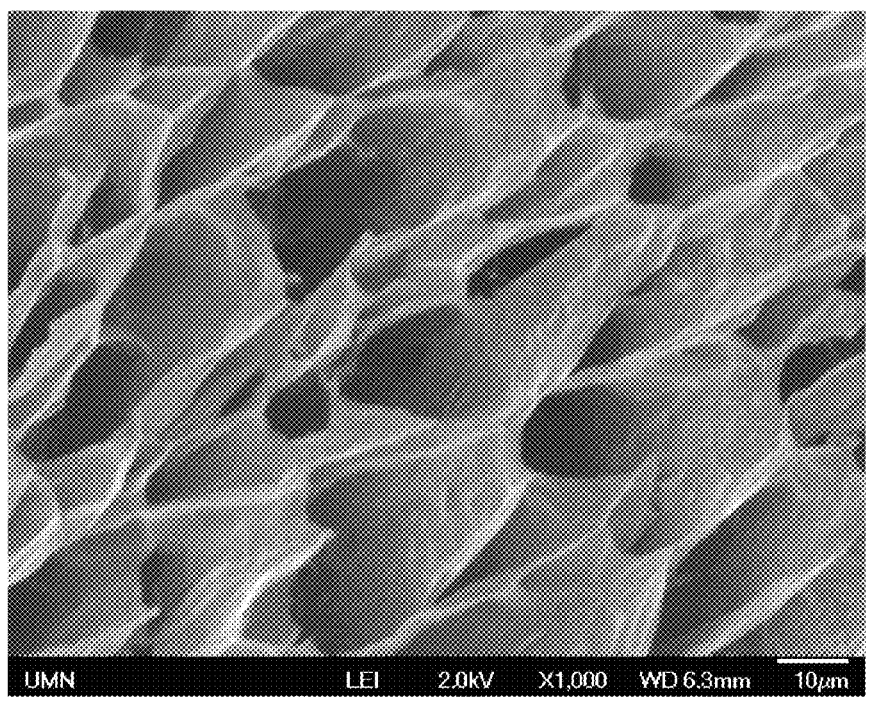

FIGS. 4A and 4B are examples of SEM images of a hydrogel prepared with CCN crosslinked with CMC in accordance with aspects of the disclosure. The hydrogel was cut to expose an interior of the hydrogel and reveal the porous structure of the hydrogel. The SEM images were collected using a JEOL JSM-6700 SEM. FIG. 4A was collected at 500× magnification, while FIG. 4B was collected at 1000× magnification. Because the hydrogel was prepared using CCN crosslinked with CMC, the internal structure of microspheres formed in accordance with this disclosure is expected to be similarly porous.

In some examples, in addition to being utilized as an embolizing agent, the microspheres may be used to deliver a therapeutic agent to a therapy site. The microspheres comprising CCN crosslinked with CMC may carry therapeutic agent due to functional groups on the CCN crosslinked with CMC. For example, the microspheres may be loaded with a therapeutic agent, such as a chemotherapeutic agent, and used to deliver the chemotherapeutic agent to a tumor and/or to embolize arteries that feed the tumor. In other embodiments, the microspheres may be loaded with a cell, a bioactive molecule, or another drug.

An example of a therapeutic agent that may be loaded into the microspheres is doxorubicin (available under the trade designation Adriamycin from Selleck Chemicals LLC, Houston, Tex., U.S.A.). Doxorubicin includes a protonated amino group and a plurality of hydroxyl groups, which may interact with functional groups, such as a carboxylic group, in the microsphere to bind to the microsphere via ionic interactions. While doxorubicin is provided as one example of a therapeutic agent which may be loaded into the microspheres of the present disclosure, other therapeutic agents may be used with the microspheres. For example, hydrophilic therapeutic agents may be utilized with the microspheres according to the disclosure. In particular, therapeutic agents that include at least one functional group that interacts with a carboxylic group, hydroxyl group or an aldehyde group are expected to be compatible with microspheres of the present disclosure. Examples of such therapeutic agents include irinotecan (available under the trade designation Camptosar® from Pfizer, New York, N.Y., U.S.A), ambroxol, and other therapeutic agents with at least one positively charged functional group. In some embodiments, in addition to ionic interactions between the therapeutic agent and the CCN crosslinked with CMC, the therapeutic agent may adsorb or adsorb in the microsphere.

In some embodiments, the therapeutic agent may be loaded into the microspheres during formation of the microspheres, i.e., during the crosslinking of the CCN with the partially oxidized CMC. In such embodiments, the therapeutic agent may be deposited into the emulsion along with the CCN and oxidized CMC. As the microspheres form, the therapeutic agent may load into the microspheres.

In other embodiments, the therapeutic agent may be loaded into the microspheres after formation of the microspheres. For example, the microspheres may be immersed in a solution of the therapeutic agent in a solvent, such as saline or a saline and contrast medium mixture, to load the therapeutic agent into the microsphere. In some examples, the therapeutic agent solution may have a concentration of between about 1 mg therapeutic agent per mL solvent (mg/mL) and about 2 mg/mL.

In some examples, the therapeutic agent may be loaded into the microspheres to a concentration of between about 0.3 mg therapeutic agent per mg dry microsphere (mg/mg) and about 0.75 mg/mg.

Figure 5A:
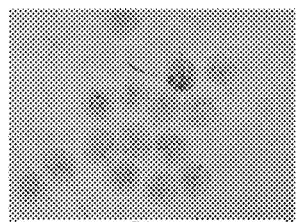
FIGS. 5A-5F are light microscopy images illustrating loading of a dye into microspheres comprising CCN crosslinked with CMC.
Figure 5B:
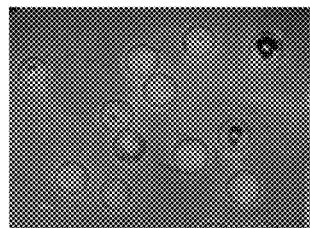
Figure 5C:
Figure 5D:
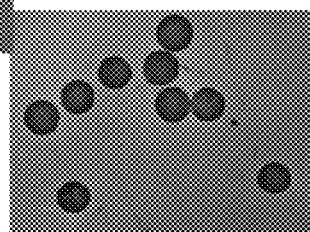
Figure 5E:
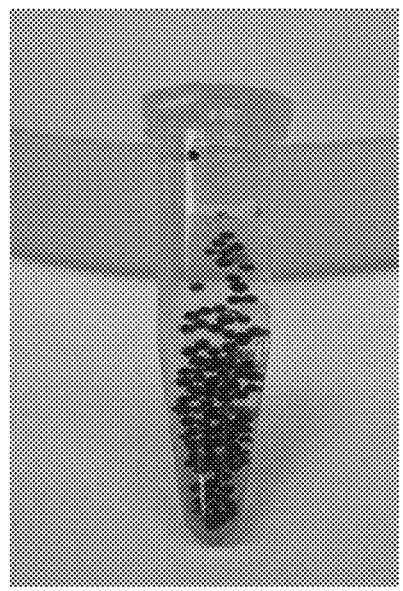
Figure 5F:
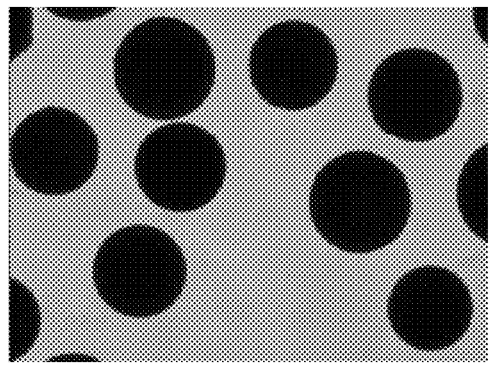

FIGS. 5A-5F are light microscopy images illustrating an example of loading a dye (Evan's blue) into microspheres comprising CCN crosslinked with CMC. FIG. 5A illustrates a plurality of microspheres suspended in normal saline prior to the dye being loaded into the microspheres. Prior to introducing the Evan's blue, saline was removed to the extent practicable using a micropipette, leaving wet microspheres. About 1 mL of a 1% w/v solution of Evan's blue in saline was added to about 50 mg wet microspheres. FIG. 5B was collected about 50 seconds after introducing the Evan's blue solution, and illustrates that loading of the dye into the microspheres has begun. FIG. 5C was taken about 4 minutes after introduction of the Evan's blue solution, and shows that additional dye has been loaded into the microspheres. FIG. 5D was collected about 16 minutes after introduction the Evan's blue solution, and shows further dye uptake by the microspheres. Finally, FIGS. 5E and 5F illustrate microspheres loaded with the dye suspended in normal saline after being removed from the Evan's blue solution.

FIGS. 6A-6C illustrate examples of microspheres according to an aspect of the disclosure after being loaded with various dyes. Specifically, FIG. 6A shows a plurality of microspheres loaded with seafoam green food coloring, FIG. 6B shows a plurality of microspheres loaded with FD&C Red Dye #40, and FIG. 6C shows a plurality of microspheres loaded with FD&C Yellow Dye #5. Prior to collecting the images shown in FIGS. 6A-6C, the microspheres were loaded with the dye in a similar manner to that described above with respect to FIGS. 5A-5F: saline was removed from a suspension of microspheres in saline using a micropipette, and about 1 mL of a 1% w/v solution of the dye in saline was added to about 50 mg wet microspheres. After loading the dye into the microspheres, the remaining dye solution was removed using a micropipette and the dye-loaded microspheres were suspended in saline. FIGS. 5A-5F and 6A-6C illustrate that the microspheres may be loaded with dyes having different functional groups, suggesting that the microspheres may also be loaded with therapeutic agent that include different functional groups.

Figure 7A:
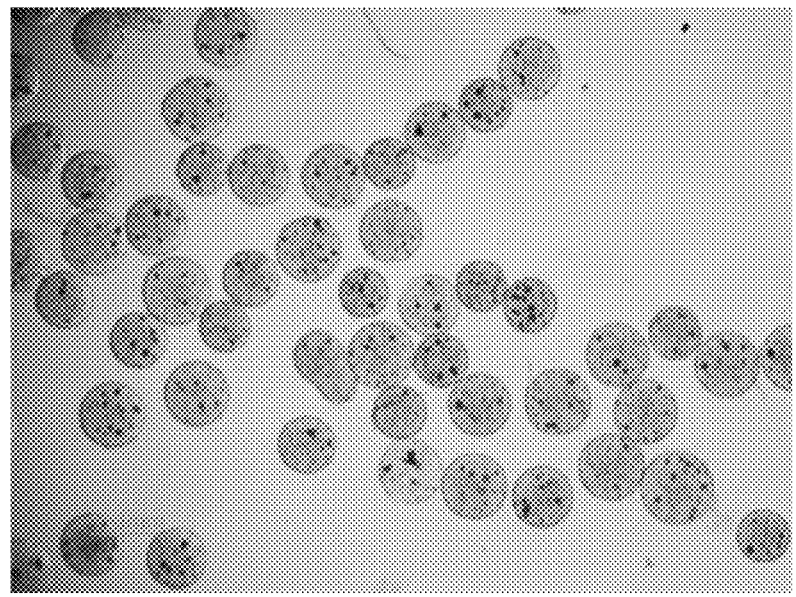
FIGS. 7A-7D are light microscopy images illustrating an example of loading doxorubicin into microspheres comprising CCN crosslinked with CMC.
Figure 7B:
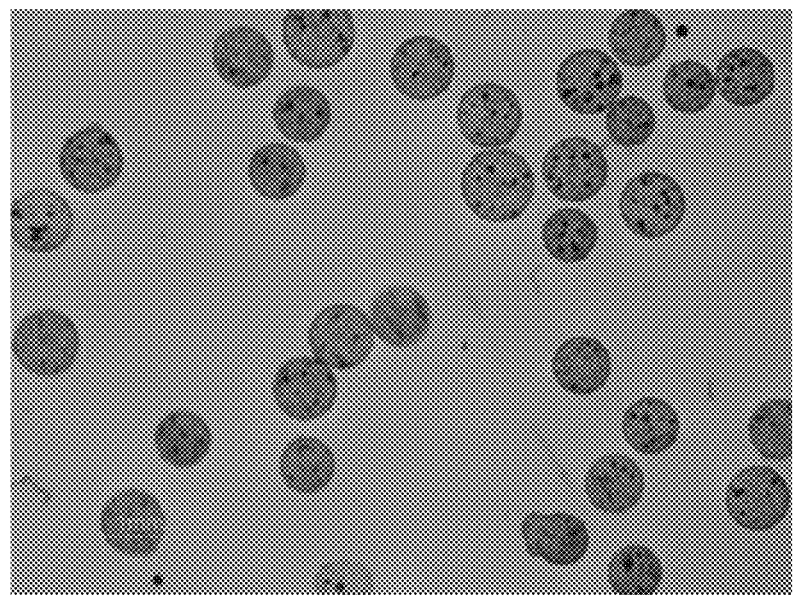
Figure 7C:
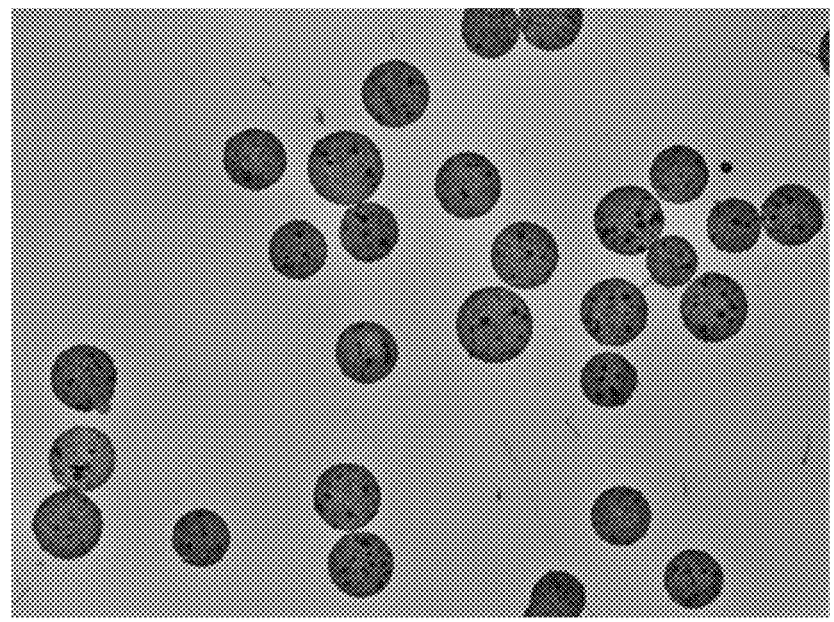
Figure 7D:
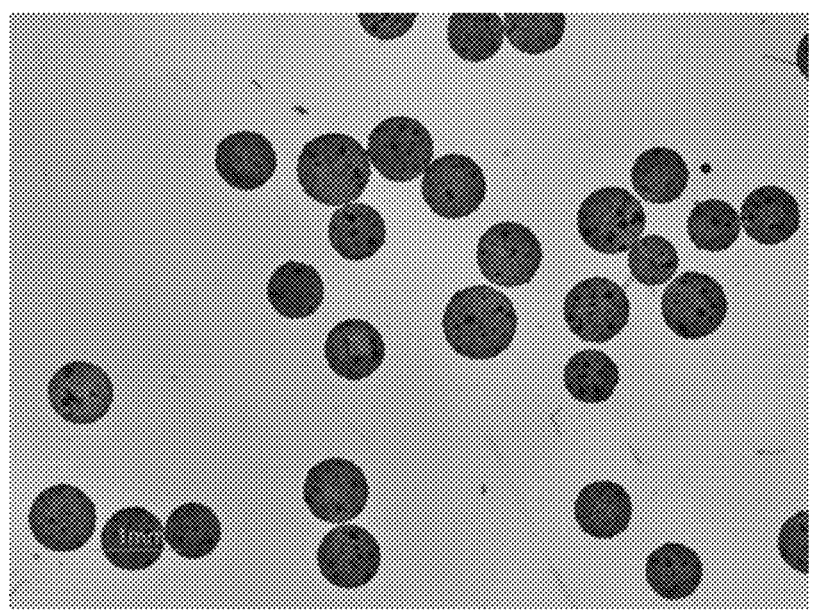
Figure 8:
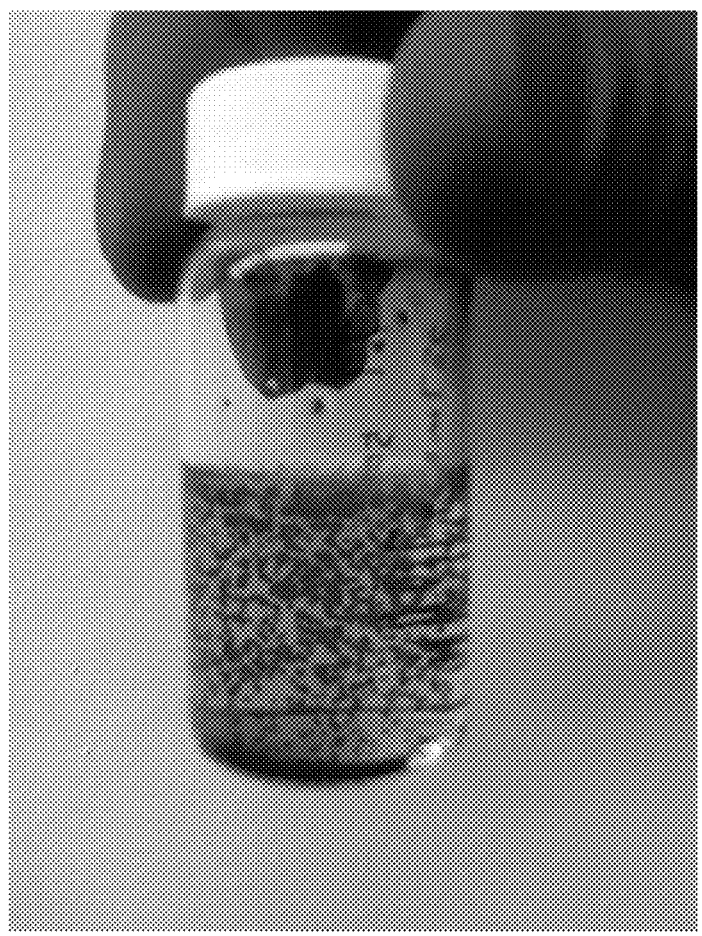
FIG. 8 is an image illustrating an example of microspheres comprising CCN crosslinked with CMC loaded with doxorubicin suspended in a solvent mixture.

FIGS. 7A-7D are images taken with a light microscope illustrating an example of loading doxorubicin into microspheres that include CCN crosslinked with CMC. FIG. 7A illustrates a plurality of microspheres suspended in normal saline prior to the doxorubicin being loaded into the microspheres. Prior to introducing the doxorubicin, saline was removed to the extent practicable using a micropipette, leaving wet microspheres. The doxorubicin solution was prepared by dissolving about 50 microliters (μL) of a commercially available doxorubicin solution (2 mg doxorubicin per mL solvent; available from Plantex USA, Woodcliff Lake, N.J., U.S.A.) in about 200 μL saline. The resulting 250 μL solution was added to about 20 mg wet microspheres. FIG. 7B was collected about 45 seconds after introducing the doxorubicin solution, and illustrates that loading of the doxorubicin into the microspheres has begun. FIG. 7C was taken about 10 minutes after introduction of the doxorubicin solution, and shows that additional doxorubicin has been loaded into the microspheres and the concentration of the doxorubicin in the medium has decreased. FIG. 7D was collected about 30 minutes after introduction the doxorubicin solution, and shows further doxorubicin uptake by the microspheres and depletion of the doxorubicin from the medium. Finally, FIG. 8 illustrates microspheres loaded with the doxorubicin suspended in a new solvent mixture (4:6, contrast:saline).

Figure 9:
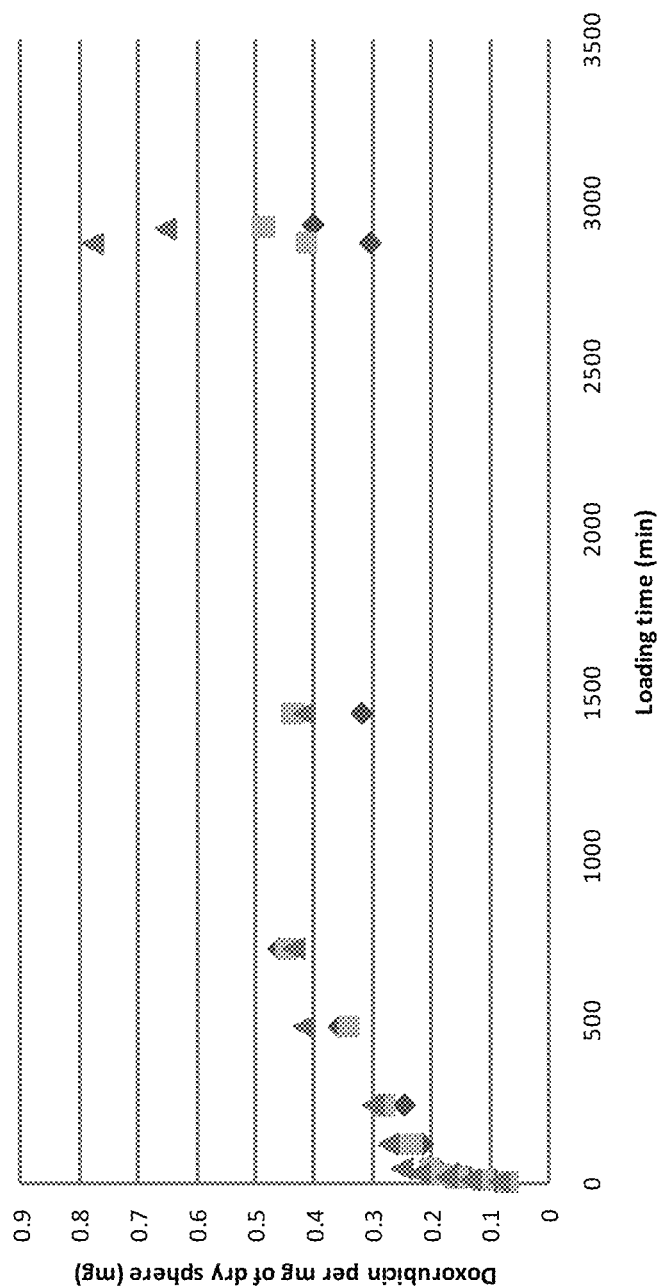
FIG. 9 is a scatter diagram illustrating examples of dynamics of loading doxorubicin into microspheres comprising CCN crosslinked with CMC of various sizes.

FIG. 9 is a scatter diagram illustrating examples of dynamics of loading doxorubicin into microspheres of various sizes. The loading of doxorubicin into the microspheres was performed in a saline medium. In FIG. 9, the triangles represent loading of doxorubicin into a plurality of microspheres having diameters of between about 300 μm and about 500 µm, the squares represent loading of doxorubicin into a plurality of microspheres having diameters between about 500 µm and about 700 µm, and the diamonds represent loading of doxorubicin into a plurality of microspheres having diameters between about 700 µm and about 850 µm. The ordinate represents the amount of doxorubicin in milligrams per milligram of dry microsphere. The abscissa represents loading time in minutes.

Figure 10:
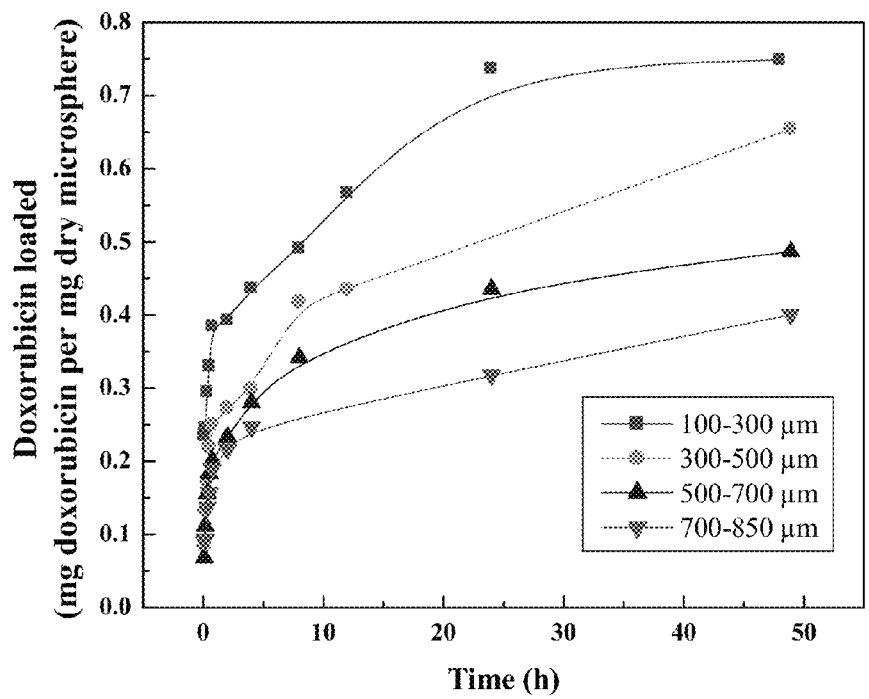
FIG. 10 is a scatter diagram illustrating examples of dynamics of loading doxorubicin into microspheres of various sizes.

FIG. 10 is a scatter diagram illustrating examples of dynamics of loading doxorubicin into microspheres of various sizes. The loading of doxorubicin into the microspheres was performed in a saline medium. In FIG. 10, the downward-pointing triangles represent loading of doxorubicin into a plurality of microspheres having diameters of between about 700 µm and about 850 µm, the upward-pointing triangles represent loading of doxorubicin into a plurality of microspheres having diameters between about 500 µm and about 700 µm, the circles represent loading of doxorubicin into a plurality of microspheres having diameters between about 300 µm and about 500 µm, and the squares represent loading of doxorubicin into a plurality of microspheres having diameters between about 100 µm and about 300 µm. Similar to FIG. 9, the ordinate represents the amount of doxorubicin in milligrams per milligram of dry microsphere. The abscissa represents loading time in hours. Both FIG. 9 and FIG. 10 show that in some embodiments a higher concentration of doxorubicin may be loaded into microspheres with smaller diameters. For example, doxorubicin may be loaded to a higher concentration in microspheres with diameters between about 100 µm and about 300 µm that in microspheres with diameters between about 700 µm and about 850 µm.

Figure 11:
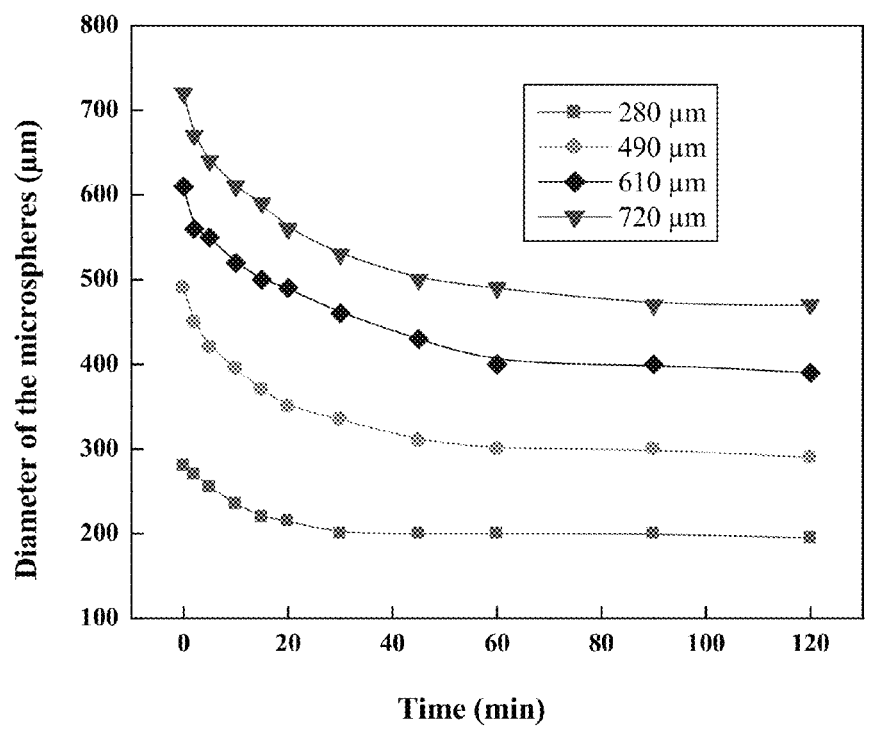
FIG. 11 is a scatter diagram that illustrates examples of changes in diameter for microspheres of different initial diameters during loading of doxorubicin.

FIG. 11 is a scatter diagram that illustrates examples of changes in diameter during loading of doxorubicin for microspheres of different initial diameters. As illustrated in FIG. 11, the diameter of the microspheres initially decreased during loading of doxorubicin and eventually reaches a substantially constant diameter. While not wishing to be bound by theory, this may be because the doxorubicin molecules include positively-charged functional groups while the microspheres are formed of CCN crosslinked with CMC, and CCN and CMC include negatively-charged functional groups. Thus, it is believed that in the absence of the doxorubicin molecules, the negatively-charged functional groups on the CCN crosslinked with CMC may repulse each other. The presence of doxorubicin in the interior of the microsphere may bring the net charge in the interior of the microsphere closer to zero, and thus may reduce electrostatic repulsion in the microsphere, which may reduce the diameter of the microsphere.

In FIG. 11, the squares represent a microsphere with an initial diameter of about 280 µm, the circles represent a microsphere with an initial diameter of about 490 µm, the diamonds represent a microsphere with an initial diameter of about 610 µm, and the triangles represent a microsphere with an initial diameter of about 720 µm.

Figure 12:
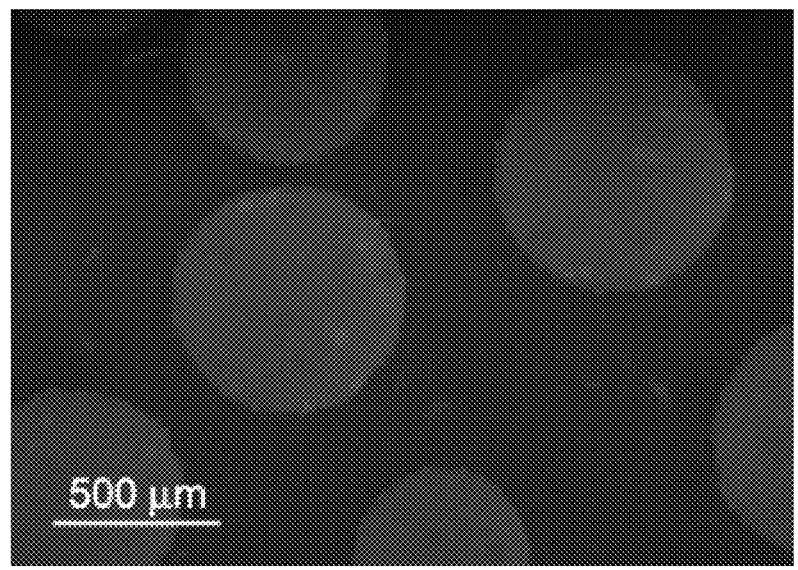
FIG. 12 is an example fluorescence microscopy image of a microsphere loaded with doxorubicin.
Figure 13:
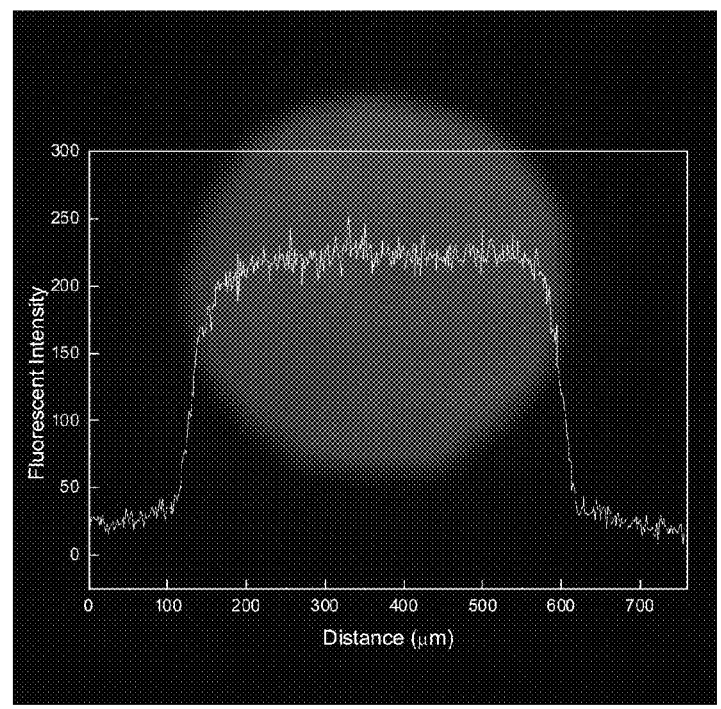
FIG. 13 is an example image illustrating fluorescence intensity as a function of distance for a single doxorubicin-loaded microsphere.

FIG. 12 is an example fluorescence microscopy image of a microsphere loaded with doxorubicin. FIG. 13 is an example image illustrating fluorescence intensity as a function of distance for a single doxorubicin-loaded microsphere. Doxorubicin fluoresces under excitation. FIG. 13 illustrates substantially similar fluorescence across the surface of the microsphere, which may suggest substantially similar doxorubicin loading across the surface of the microsphere. The microspheres illustrated in FIGS. 12 and 13 were formed of CCN crosslinked with partially oxidized CMC.

Figure 14:
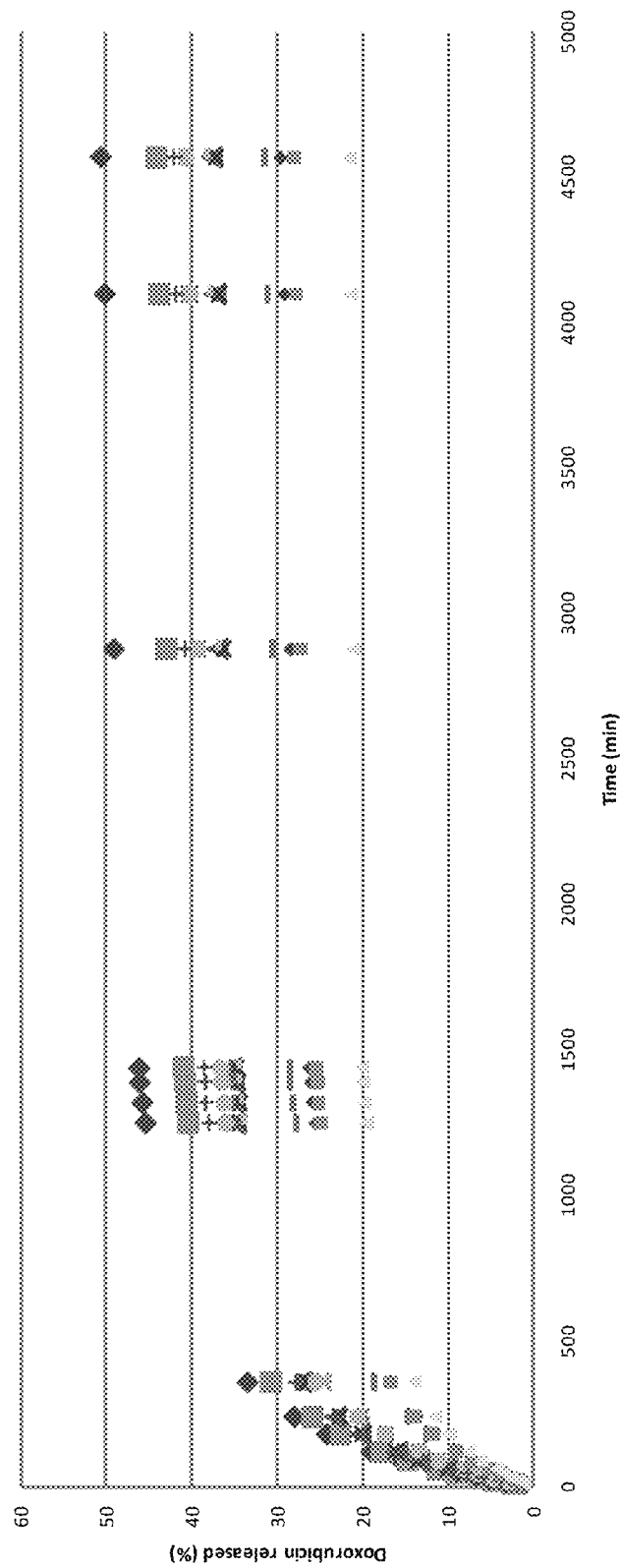
FIG. 14 is a scatter diagram illustrating examples of a percentage of doxorubicin released as a function to time for each of a plurality of samples of microspheres having different characteristics in accordance with the disclosure.

FIG. 14 is a scatter diagram illustrating an example of a percentage of doxorubicin released as a function of time, measured in minutes, for each of a plurality of samples of microspheres having different characteristics. Each of the samples was disposed in about 2 mL saline for the duration of the measurement. The saline was not changed during the measurement. The different samples of microspheres included different diameter ranges and different initial weights (total initial weight of microspheres loaded with doxorubicin). For example, four of the samples included microspheres with diameters between about 300 µm and about 500 µm. For a first of these samples, represented by the smaller upward-pointing triangles, the plurality of microspheres had an average initial weight of about 5.3 mg; a second of these samples, represented by smaller squares, included a plurality of microspheres having an average initial weight of about 3.7 mg; a third of these samples, represented by the smaller diamonds, included a plurality of microspheres having an average initial weight of about 3.6 mg; and a fourth of these samples, represented by longer horizontal lines, included a plurality of microspheres having an average initial weight of about 3.3 mg.

Four additional samples included microspheres with diameters between about 500 µm and about 700 µm. For a first of these samples, represented by shorter horizontal lines, the plurality of microspheres had an average initial weight of about 4.5 mg; a second of these samples, represented by crosses, included a plurality of microspheres having an average initial weight of about 4 mg; a third of these samples, represented by circles, included a plurality of microspheres having an average initial weight of about 3.5 mg; and a fourth of these samples, represented by asterisks, included a plurality of microspheres having an average initial weight of about 3.2 mg.

An additional four samples included microspheres with diameters between about 700 µm and about 850 µm. For a first of these samples, represented by x's, the plurality of microspheres had an average initial weight of about 5 mg; a second of these samples, represented by the larger upward-pointing triangles, included a plurality of microspheres having an average initial weight of about 4.9 mg; a third of these samples, represented by the larger squares, included a plurality of microspheres having an average initial weight of about 3.2 mg; and a fourth of these samples, represented by larger diamonds, included a plurality of microspheres having an average initial weight of about 3 mg.

Figure 15:
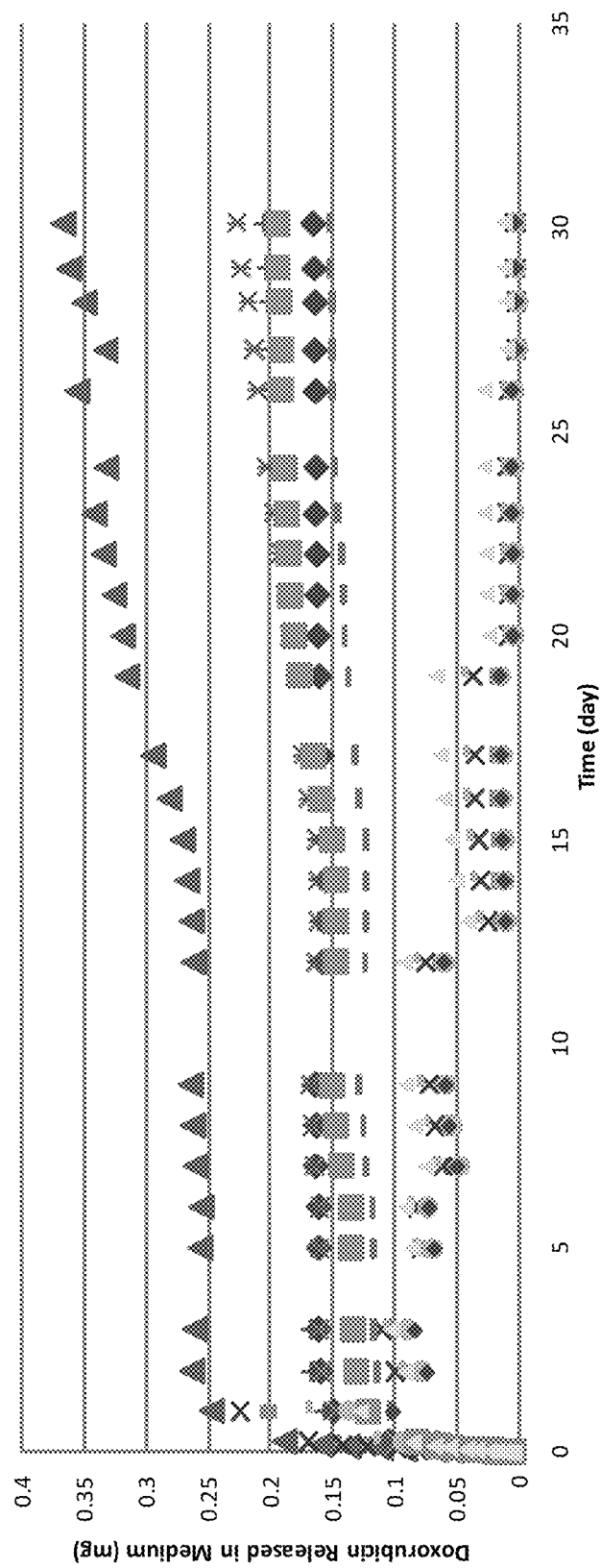
FIG. 15 is a scatter diagram illustrating examples of an amount of doxorubicin released as a function to time for each of a plurality of samples of microspheres having different characteristics in accordance with the disclosure.

FIG. 15 is a scatter diagram illustrating examples of an amount of doxorubicin in milligrams released as a function of time, measured in days, for each of a plurality of samples of microspheres having different characteristics. Each of the samples was disposed in a cuvette filled with about 2 mL saline. For some of the samples, the microspheres were disposed in the same volume of saline for the duration of the measurement. For other samples, the saline in which the microspheres loaded with doxorubicin were disposed was changed periodically. In particular, the saline was changed after 1 day, 3 days, 6 days, 12 days, 19 days, and 26 days. Additionally, in the samples in which the saline was changed periodically, the cuvette in which the microspheres and saline were disposed was changed after 12 days and after 26 days.

The different samples of microspheres included different diameter ranges and different initial weights (of the microspheres loaded with doxorubicin). For example, four of the samples included microspheres with diameters between about 300 µm and about 500 µm. A first of these samples, represented by smaller upward-pointing triangles, included a plurality of microspheres having an average initial weight of about 4.8 mg (the saline in which the first sample was disposed was changed as described above). A second of these samples, represented by larger squares, included a plurality of microspheres having an average initial weight of about 4.3 mg (the saline in which the second sample was disposed was not changed). A third of these samples, represented by smaller diamonds, included a plurality of microspheres having an average initial weight of about 3.3 mg (the saline in which the third sample was disposed was changed as described above). A fourth of these samples, represented by longer horizontal lines, included a plurality of microspheres having an average initial weight of about 3.1 mg (the saline in which the fourth sample was disposed was not changed).

Four more samples illustrated in FIG. 15 included microspheres with diameters between about 500 μm and about 700 μm. A first of these samples, represented by shorter horizontal lines, included a plurality of microspheres having an average initial weight of about 4.8 mg (the saline in which the first sample was disposed was changed as described above). A second of these samples, represented by crosses, included a plurality of microspheres having an average initial weight of about 4.5 mg (the saline in which the second sample was disposed was not changed). A third of these samples, represented by circles included a plurality of microspheres having an average initial weight of about 3.7 mg (the saline in which the third sample was disposed was changed as described above). A fourth of these samples, represented by asterisks, included a plurality of microspheres having an average initial weight of about 3.4 mg (the saline in which the fourth sample was disposed was not changed).

An additional four samples shown in FIG. 15 included microspheres with diameters between about 700 μm and about 850 μm. A first of these samples, represented by x's, included a plurality of microspheres having an average initial weight of about 4.5 mg (the saline in which the first sample was disposed was changed as described above). A second of these samples, represented by larger, upward-pointing triangles, included a plurality of microspheres having an average initial weight of about 4.2 mg (the saline in which the second sample was disposed was not changed). A third of these samples, represented by smaller squares, included a plurality of microspheres having an average initial weight of about 4.0 mg (the saline in which the third sample was disposed was changed as described above). A fourth of these samples, represented by larger diamonds, included a plurality of microspheres having an average initial weight of about 3.2 mg (the saline in which the fourth sample was disposed was not changed).

Figure 16:
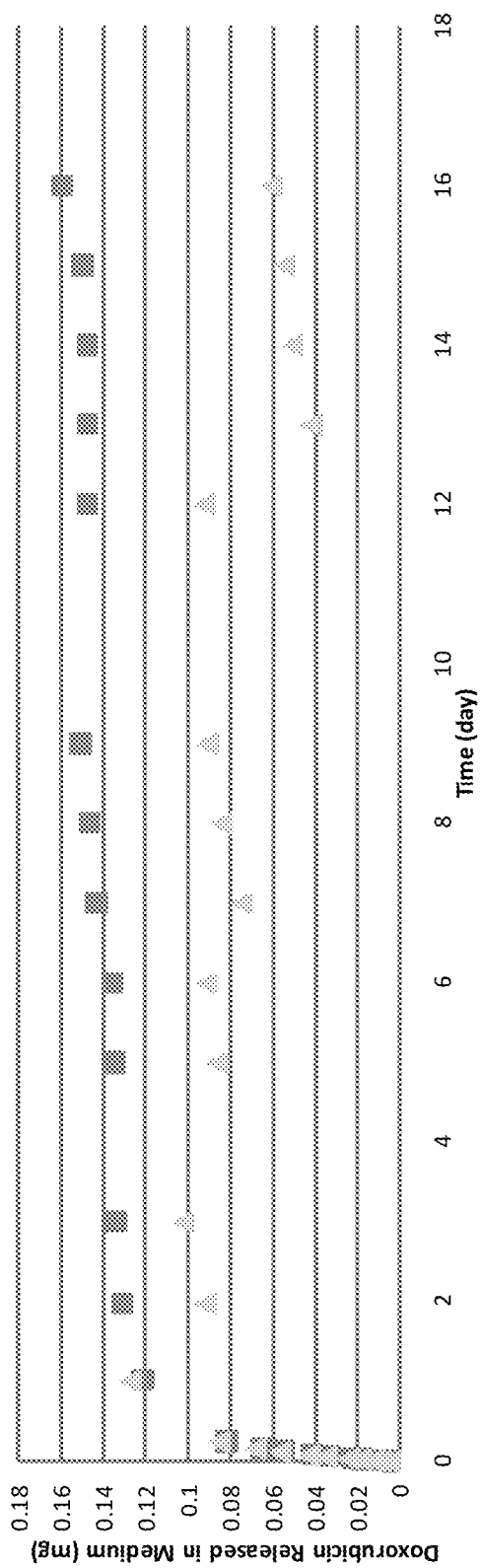
FIG. 16 is a scatter diagram illustrating examples of an amount of doxorubicin released in a saline medium as a function of time for each of a plurality of samples of microspheres having different characteristics in accordance with the disclosure.

FIG. 16 is a scatter diagram illustrating examples of an amount of doxorubicin released in a saline medium as a function to time, measured in days, for each of a plurality of samples of microspheres having different characteristics. Each of the samples was disposed in a cuvette filled with 2 mL saline. For the first sample, the plurality of microspheres had diameters between about 300 μm and about 500 μm and the microspheres had an initial average initial weight of about 4.3 mg (the weight of the microspheres loaded with doxorubicin). The first sample, represented by squares, was disposed in the same saline for the duration of the measurement. For the second sample, represented by triangles, the saline in which the microspheres loaded with doxorubicin were disposed was changed periodically. In particular, the saline was changed after 1 day, 3 days, 6 days, 12 days, 19 days, and 26 days. Additionally, the cuvette in which the second sample was disposed was changed after 12 days and after 26 days. The second sample included microspheres with a diameter of between about 300 μm and about 500 μm and the microspheres had an average initial weight of about 4.8 mg.

Figure 17:
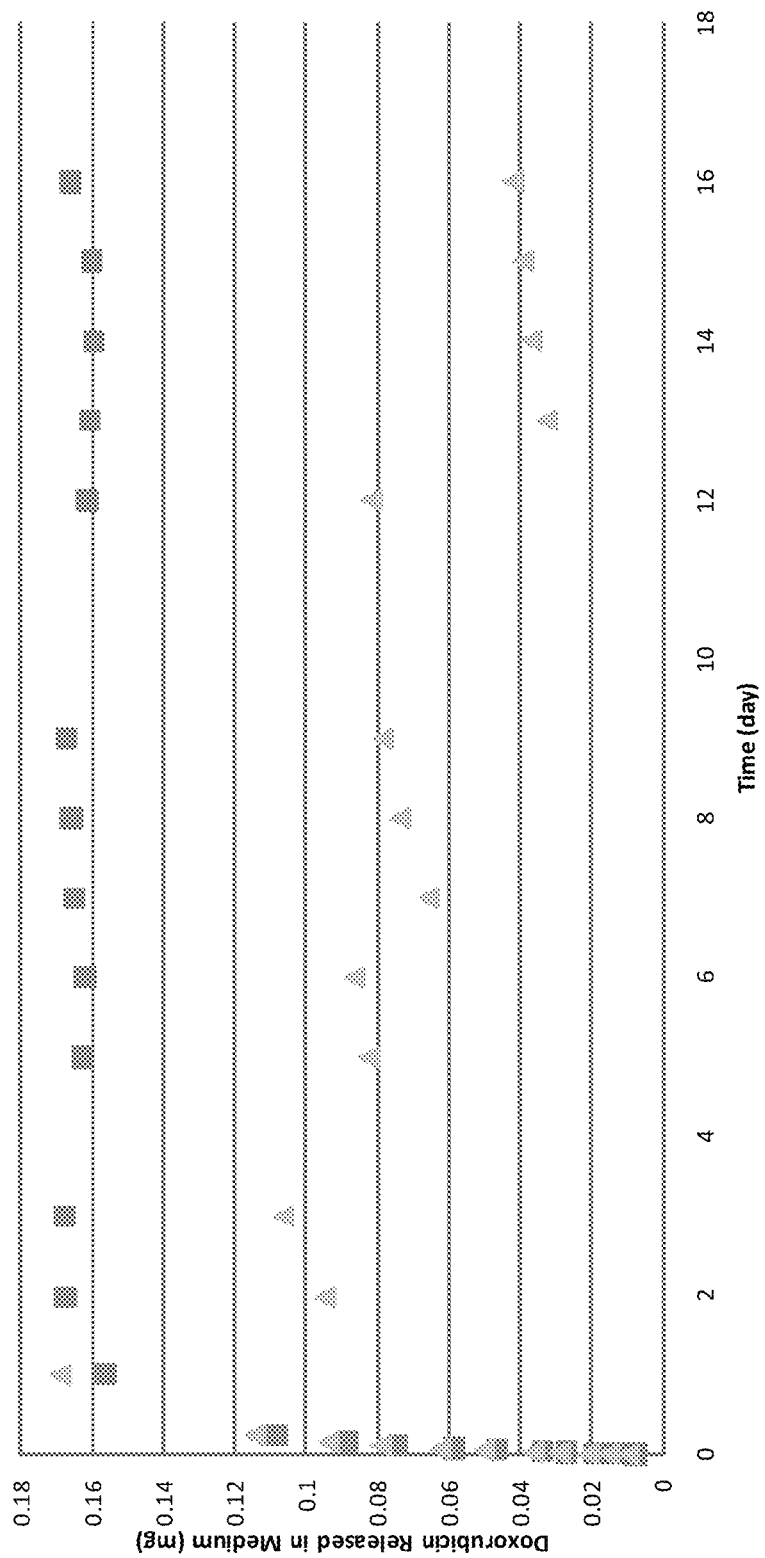
FIG. 17 is a scatter diagram illustrating examples of an amount of doxorubicin released in a saline medium as a function of time for each of a plurality of samples of microspheres having different characteristics in accordance with the disclosure.

FIG. 17 is a scatter diagram illustrating examples of an amount of doxorubicin released in a saline medium as a function to time, measured in days, for each of a plurality of samples of microspheres having different characteristics. Each of the samples was disposed in a cuvette filled with 2 mL saline. For the first sample, represented by squares, the plurality of microspheres had a diameter between about 500 μm and about 700 μm and was loaded with doxorubicin to an average initial weight of about 4.5 mg. The first sample was disposed in the same saline for the duration of the measurement. For the second sample, the saline in which the microspheres loaded with doxorubicin were disposed was changed periodically. In particular, the saline was changed after 1 day, 3 days, 6 days, 12 days, 19 days, and 26 days. Additionally, the cuvette in which the second sample was disposed was changed after 12 days and after 26 days. The second sample included microspheres with a diameter of between about 500 μm and about 700 μm and the microspheres were loaded with doxorubicin to an average initial weight of about 4.8 mg.

Figure 18:
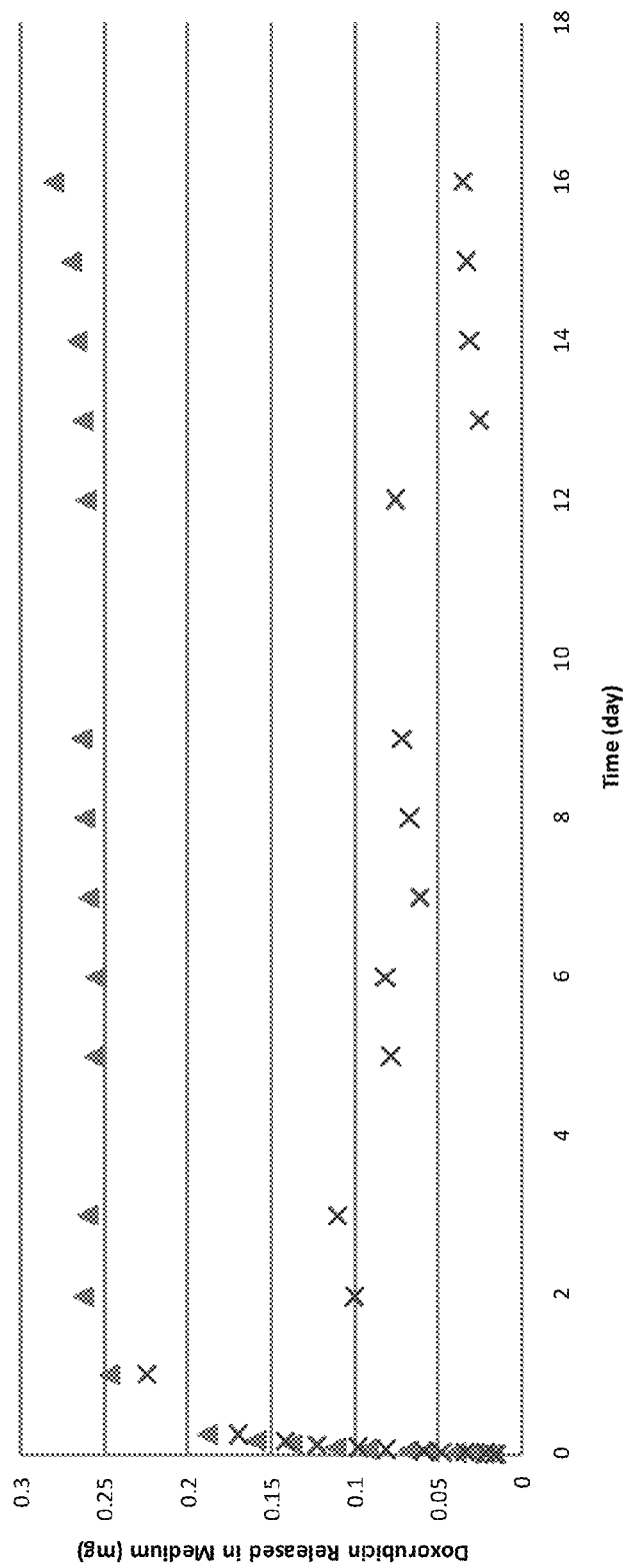
FIG. 18 is a scatter diagram illustrating examples of an amount of doxorubicin released in a saline medium as a function of time for each of a plurality of samples of microspheres having different characteristics in accordance with the disclosure.

FIG. 18 is a scatter diagram illustrating examples of an amount of doxorubicin released in a saline medium as a function to time, measured in days, for each of a plurality of samples of microspheres having different characteristics. Each of the samples was disposed in a cuvette filled with 2 mL saline. For the first sample, represented by upward-pointing triangles, the plurality of microspheres had a diameter between about 700 μm and about 850 μm and was loaded with doxorubicin to a total average initial weight of about 4.2 mg. The first sample was disposed in the same saline for the duration of the measurement. For the second sample, the saline in which the microspheres loaded with doxorubicin were disposed was changed periodically. In particular, the saline was changed after 1 day, 3 days, 6 days, 12 days, 19 days, and 26 days. Additionally, the cuvette in which the second sample was disposed was changed after 12 days and after 26 days. The second sample, represented by x's, included microspheres with a diameter of between about 700 μm and about 850 μm and the microspheres were loaded to a total average initial weight of about 4.5 mg.

Figure 19:
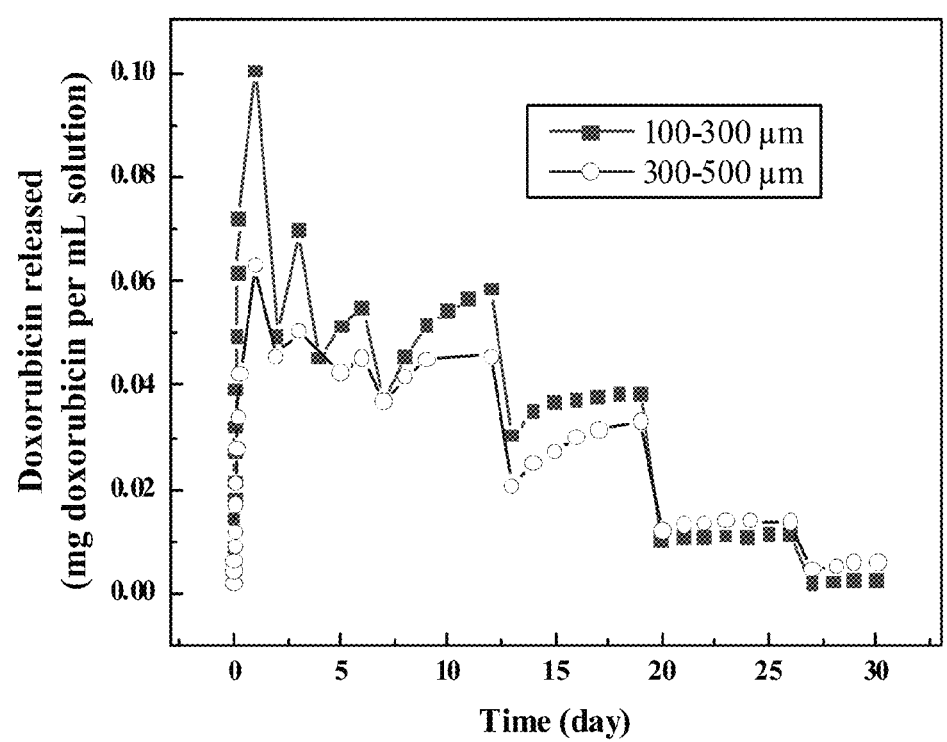
FIG. 19 is a line diagram that illustrates an example comparison of doxorubicin release rate between microspheres of two different diameter ranges.

FIG. 19 is a line diagram that illustrates an example comparison of doxorubicin release rate between microspheres of two different diameter ranges. Each of the samples was placed in a cuvette filled with about 2 mL normal saline and the concentration of the doxorubicin in the saline was measured periodically. The saline in which the microspheres loaded with doxorubicin were disposed was changed after 1 day, 3 days, 6 days, 12 days, 19 days, and 26 days. Additionally, the cuvettes in which the samples were disposed were changed after 12 days and after 26 days. The first sample, represented by squares in FIG. 19, included microspheres with diameters between about 100 μm and about 300 μm. The initial weight of the 100 μm to 300 μm microspheres was about 4.4 mg. The second sample, represented by open circles in FIG. 19, included microspheres with diameters between about 300 μm and about 500 μm. The initial weight of the 300 μm to 500 μm microspheres was about 4.8 mg. FIG. 19 shows that in this example, the larger microspheres initially release the doxorubicin somewhat slower than the smaller microspheres, but the larger microspheres provided a somewhat more sustained release of the doxorubicin (e.g., after about 20 days).

Figure 20:
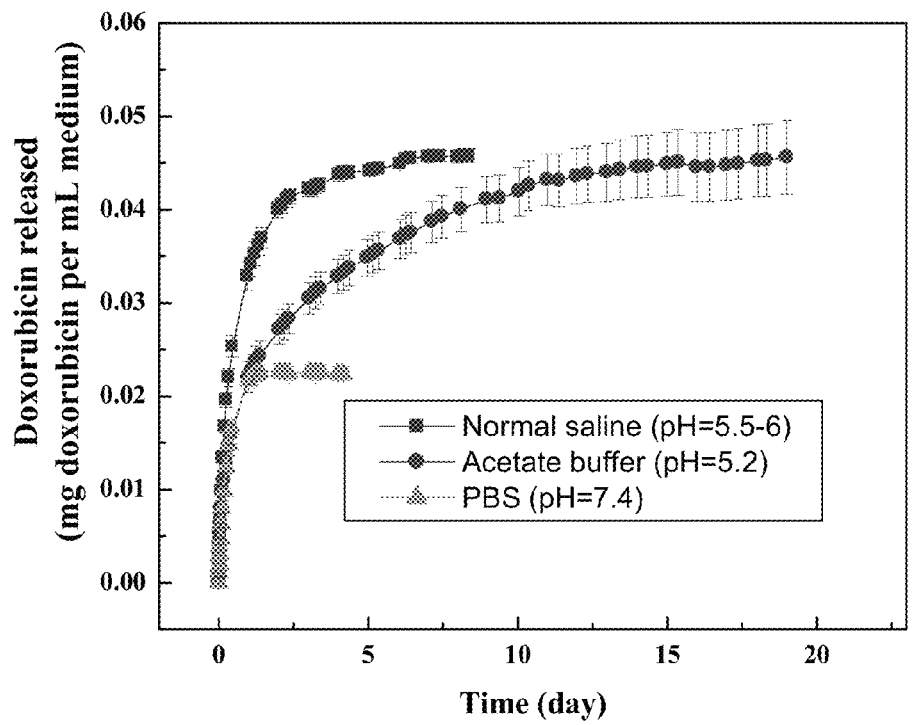
FIG. 20 is a line diagram that illustrates examples of release of doxorubicin from microspheres in different media.

FIG. 20 is a line diagram that illustrates examples of release of doxorubicin from microspheres in different media. The data points illustrated as squares in FIG. 20 represent release of doxorubicin from microspheres placed in normal saline, which had a pH of between about 5.5 and 6.0. The data points illustrated as circles in FIG. 20 represent release of doxorubicin from microspheres placed in acetate buffered saline, which had a pH of about 5.2. The data points illustrated as triangles in FIG. 20 represent release of doxorubicin from microspheres placed in PBS, which had a pH of about 7.4. The medium was not changed for any of the samples during the duration of the testing.

In each of the samples, the diameters of the microspheres were between about 300 μm and about 500 μm. Each of the microspheres was initially loaded with about 0.22 mg doxorubicin. In FIG. 20, the concentration of doxorubicin in the medium, measured in mg doxorubicin per mL medium, is plotted as a function of time, measured in days.

FIG. 20 shows that in this example, a greater amount of doxorubicin was generally released from the microspheres when the surrounding medium had a lower pH. For example, the microspheres in the PBS medium, which had the highest pH, released doxorubicin to a concentration in the medium of less than about 0.025 mg/mL. In the acetate buffered saline and the normal saline, doxorubicin was released from the microspheres to a concentration in the medium of about 0.045 mg/mL.

Figure 21:
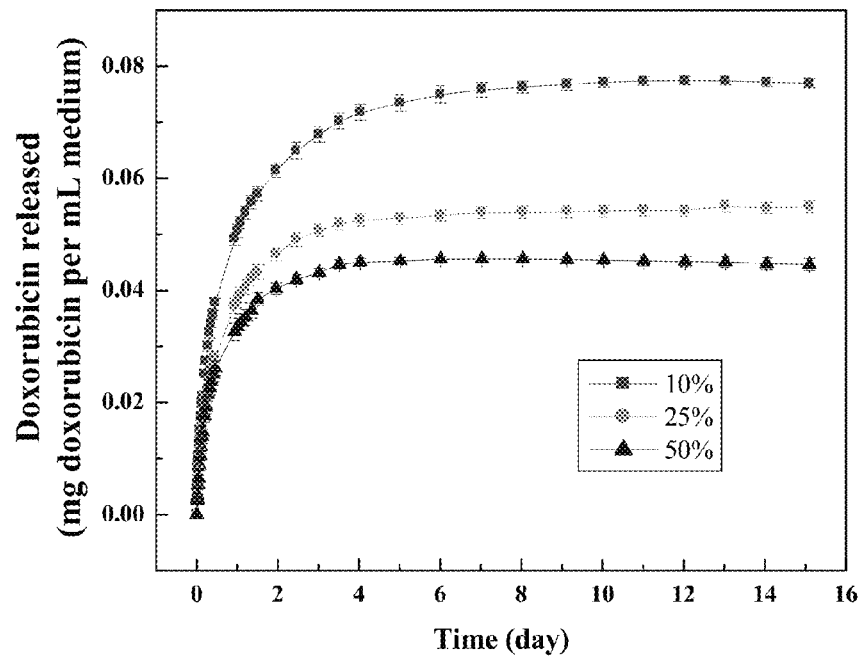
FIG. 21 is a line diagram that illustrates an example of the effect the degree of oxidation of the CMC may have on the release rate of doxorubicin from microspheres that are formed of CCN crosslinked with CMC.

As described above, the degree of oxidation of the CMC may be controlled in the initial oxidizing reaction when preparing partially oxidized CMC. The degree of oxidation may be defines as the number of repeating units oxidized per 100 repeating units. As described above, CMC with a higher degree of oxidation may result in more crosslinks when reacted with CCN. FIG. 21 is a line diagram that illustrates an example of the effect the degree of oxidation of the CMC may have on the release rate of doxorubicin from microspheres that are formed of CCN crosslinked with CMC. In FIG. 21, the concentration of doxorubicin in the medium, measured in mg doxorubicin per mL medium, is plotted as a function of time, measured in days. The microspheres in each sample had diameters between about 300 μm and about 500 μm, and each sample of the microspheres was initially loaded with an average of about 0.50 mg doxorubicin.

The data points illustrated in FIG. 21 by squares represent the doxorubicin released from microspheres formed of CCN crosslinked with CMC with a degree of oxidation of about 10% (i.e., about 1 in 10 repeating units of the CMC was oxidized). The data points illustrated in FIG. 21 by circles represent the doxorubicin release from microspheres formed of CCN crosslinked with CMC with a degree of oxidation of about 25%. The data points illustrated in FIG. 21 by triangles represent the doxorubicin release from microspheres formed of CCN crosslinked with CMC with a degree of oxidation of about 50%. Thus, FIG. 21 illustrates that in this example, a greater amount of doxorubicin was released from the microspheres formed of CCN crosslinked with CMC with a lower degree of oxidation (correlating with a lower crosslinking density).

Figure 22:
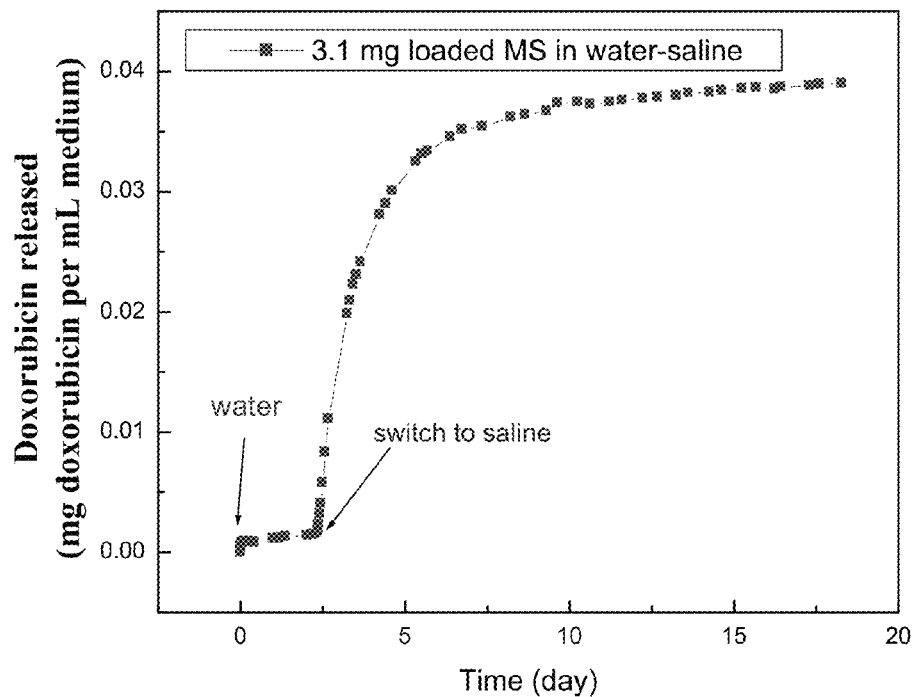
FIG. 22 is a line diagram that illustrates an example of the effect of the medium on the release of doxorubicin from the microspheres.

FIG. 22 is a line diagram that illustrates an example of the effect of the medium on the release of doxorubicin from microspheres formed of CCN crosslinked with CMC. In FIG. 22, the concentration of doxorubicin in the medium, measured in mg doxorubicin per mL medium, is plotted as a function of time, measured in days. The microspheres were formed of CCN crosslinked with CMC, and had diameters between about 300 μm and about 500 μm. The average initial weight of the microspheres was about 3.1 mg (including doxorubicin), and about 0.18 mg of the weight was doxorubicin. As shown in FIG. 22, the microspheres were initially placed in a water medium, and little doxorubicin was released from the microspheres formed of CCN crosslinked with CMC. However, after about two and one half days, the microspheres were placed in a saline medium, and doxorubicin began being released from the microspheres in greater amounts. This may suggest that ion exchange plays a role in the release of doxorubicin from the microspheres formed of CCN crosslinked with CMC.

Figure 23:
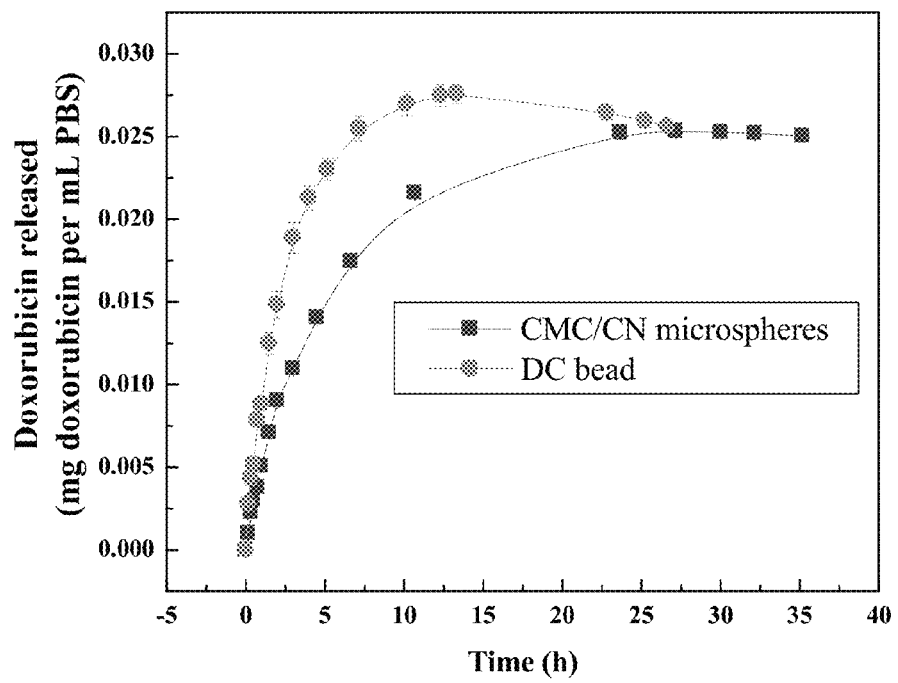
FIG. 23 is a line diagram that illustrates an example comparison between release rates of doxorubicin from microspheres according to an aspect the current disclosure and DC Beads™.

FIG. 23 is a line diagram that illustrates an example comparison between release rates of doxorubicin from microspheres according to an aspect the disclosure and DC Beads™, a polyvinyl alcohol-based embolization bead available from Biocompatibles, Farnham, Surrey, United Kingdom. The microspheres formed of CCN crosslinked with CMC had diameters between about 300 μm and about 500 μm, and initial doxorubicin loading was about 0.50 mg. The DC Beads™ also had diameters between about 300 μm and about 500 μm, and were loaded with an average of about 0.50 mg doxorubicin. Each of the samples was placed in PBS for the duration of the testing. In FIG. 23, the concentration of doxorubicin in the PBS, measured in mg doxorubicin per mL PBS, is plotted as a function of time, measured in hours. In this example, the release of doxorubicin from the CCN crosslinked with CMC microspheres may be more gradual and sustained than the release of doxorubicin from the DC Beads™ microspheres.

Figure 24:
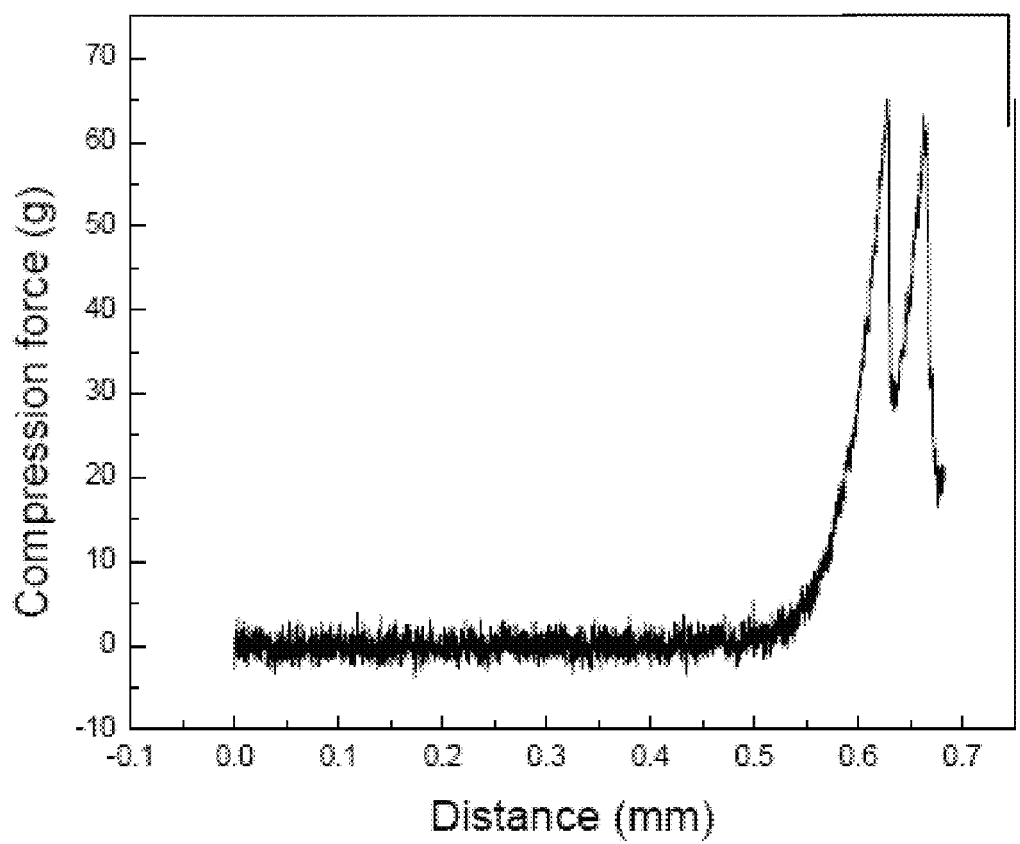
FIG. 24 is an example of a plot of compression force versus distance for a single microsphere having a diameter of about 715 μm.

In some embodiments, regardless of whether the microspheres are loaded with drug, the microspheres comprising CCN crosslinked with CMC may have advantageous mechanical properties. For example, the microspheres may be compressible, and may substantially return to their original shape after being compressed. FIG. 24 is a plot of compression force versus distance for a single microsphere having a diameter of about 715 μm and a crosslinking density of about 10%. The compression test was performed using a TA.XTPlus Texture Analyzer (Texture Technologies Corp., Scarsdale, N.Y.). The microsphere was compressed at a rate of about 0.08 mm/s. As illustrated in FIG. 24, the microsphere compresses about 622 μm (0.622 mm) before irreversibly deforming, resulting in a fracture strain of about 87%. Additionally, the compression force at fracture was about 65.5 g. As described above, the fracture strain may be adjusted between about 70% and about 90% by controlling a crosslinking density between the CCN and CMC.

Figure 25A:
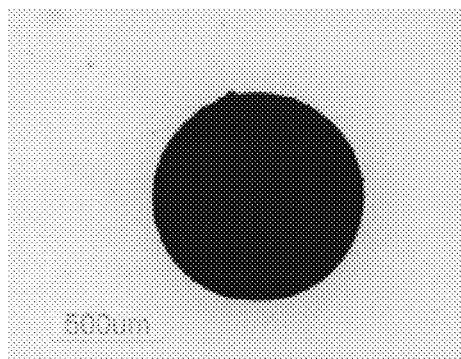
FIGS. 25A-25C are light microscopy images illustrating an example of the compressibility of a microsphere comprising CCN crosslinked with CMC (dyed with Evan's blue) as the microsphere passes through a polyethylene tube.
Figure 25B:
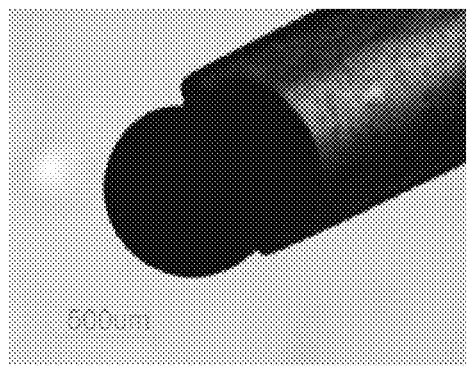
Figure 25C:
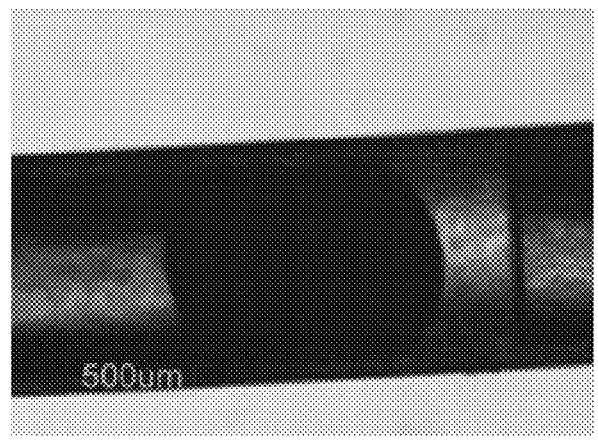

FIGS. 25A-25C are light microscopy images illustrating an example of the compressibility of a microsphere comprising CCN crosslinked with CMC as the microsphere passes through a polyethylene tube. The microsphere has a diameter of about 925 μm and the catheter has an internal diameter of about 580 μm (PE-50). As FIGS. 25B and 25C illustrate, the microsphere can deform and pass through the internal cavity of the catheter.

Figure 26A:
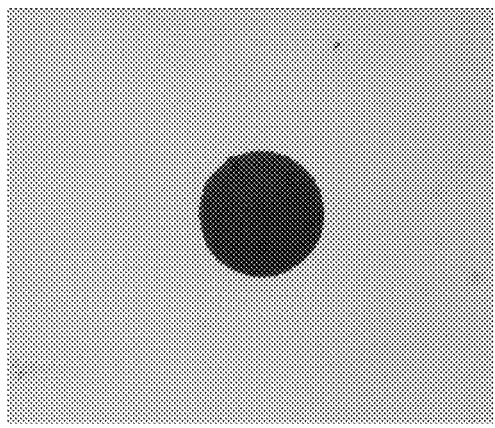
FIGS. 26A-26C are light microscopy images that illustrate another example of the compressibility of a microsphere comprising CCN crosslinked with CMC (dyed with Evan's blue) as the microsphere passes through a polyethylene tube.
Figure 26B:
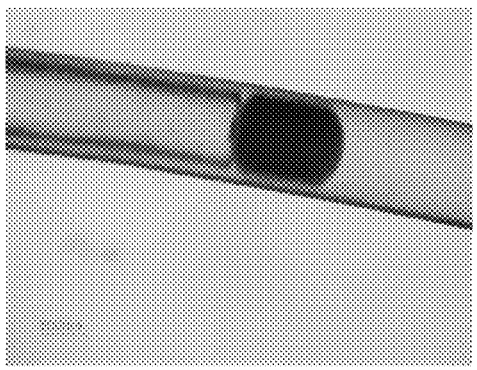
Figure 26C:
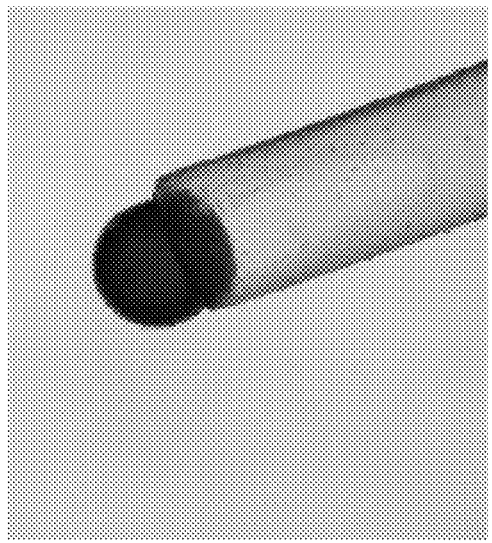

FIGS. 26A-26C are light microscopy images that illustrate another example of the compressibility of a microsphere comprising CCN crosslinked with CMC and having a diameter of about 860 μm as the microsphere passes through a polyethylene tube. In FIGS. 26A-26C, the catheter again has an internal diameter of about 580 μm (PE-50). As FIGS. 26B and 26C illustrate, the microsphere can reversibly deform, pass through the internal cavity of the catheter, and return to a shape and size substantially similar to the shape and size of the microsphere before passing through the catheter.

FIGS. 27A and 27B illustrate an example of the resiliency of a microsphere comprising CCN crosslinked with CMC.

The microsphere pictured in FIGS. 27A and 27B has a diameter of about 675 µm and was disposed in a polyethylene tube with an internal diameter of about 580 µm (PE-50) for about 24 hours prior to being released. The image shown in FIG. 27A was collected about 3 seconds after the microsphere was released from the PE tube, and the image shown in FIG. 27B was collected about 5 seconds after the microsphere was released. FIGS. 27A and 27B illustrate that the microsphere may recover its spherical shape and original size relatively quickly after being released from the PE tube.

FIG. 28 is a light microscopy image of an example of microspheres having diameters between about 500 µm and about 700 µm taken after the microspheres were injected through a catheter with an internal diameter of about 480 µm (2 French catheter, available from Boston Scientific Corp., Natick, Mass.). As illustrated in FIG. 28, the microspheres substantially retained their original, spherical shape.

Figure 29A:
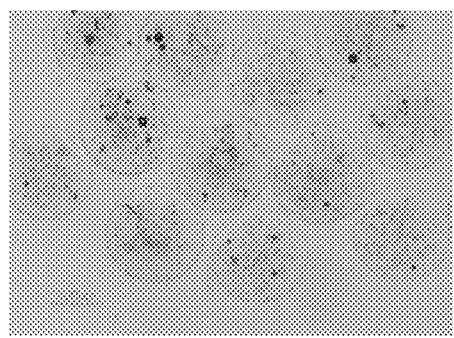
FIGS. 29A and 29B are light microscopy images of an example of microspheres comprising CCN crosslinked with CMC and having diameters between about 800 μm and about 1000 μm after being injected through a catheter with an internal diameter of about 1 mm (3 French).
Figure 29B:
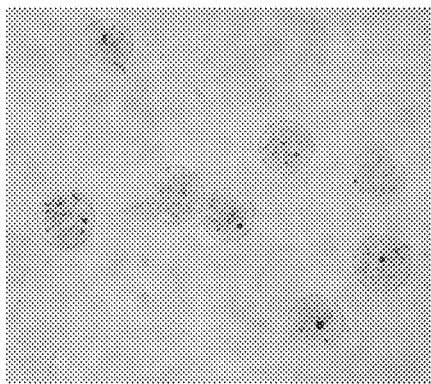

FIGS. 29A and 29B are light microscopy images of an example of microspheres having diameters between about 800 µm and about 1000 µm taken after the microspheres were injected through a catheter with an internal diameter of about 0.53 mm (3 French catheter, Terumo Medical Corp., Somerset, N.J.). As illustrated in FIGS. 29A and 29B, the microspheres substantially retained their original, spherical shape.

Figure 30A:
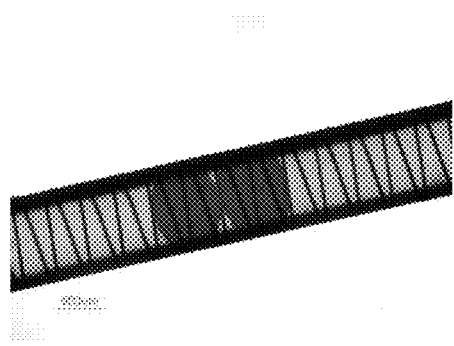
FIGS. 30A and 30B are light microscopy images of an example of microspheres comprising CCN crosslinked with CMC and loaded with doxorubicin while passing through a catheter and after passing through the catheter.
Figure 30B:
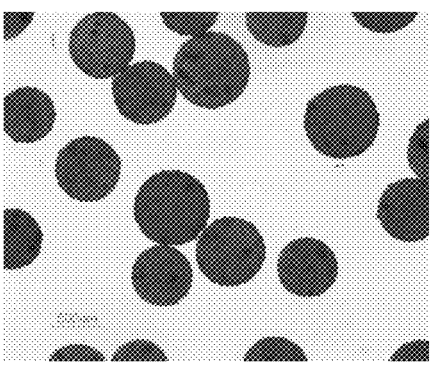

FIGS. 30A and 30B are light microscopy images of an example of microspheres loaded with doxorubicin while passing through a catheter and after passing through the catheter. The microspheres illustrated in FIGS. 30A and 30B have a diameter between about 500 µm and about 700 µm. The catheter shown in FIG. 30A had an internal diameter of about 0.53 mm (3 French catheter, Terumo Medical Corp., Somerset, N.J.). As shown in FIG. 30B, the microspheres substantially retained their original, spherical shape.

Figure 31A:
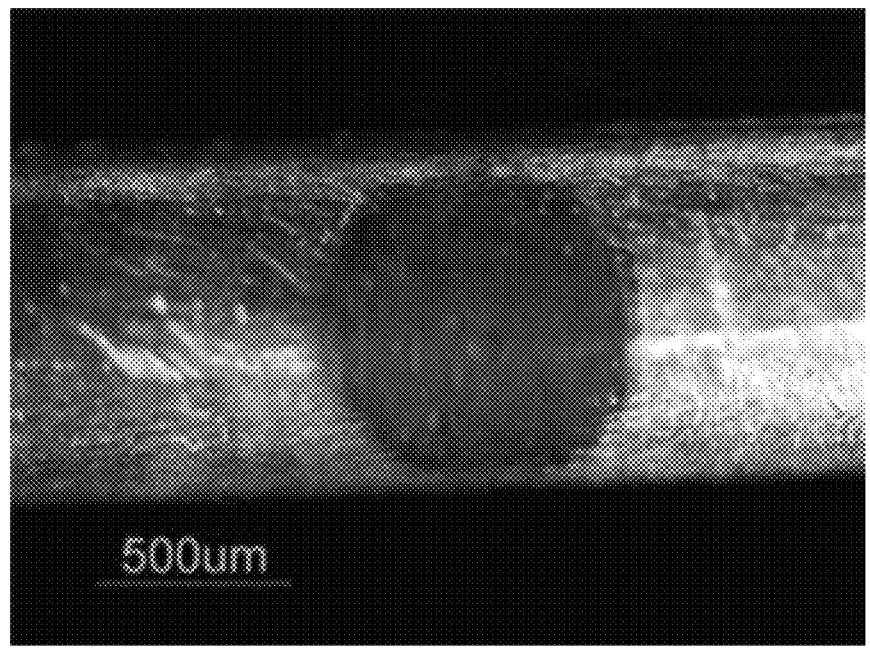
FIGS. 31A and 31B are light microscopy images of an example of microspheres comprising CCN crosslinked with CMC and loaded with doxorubicin while passing through a polyethylene tube.
Figure 31B:
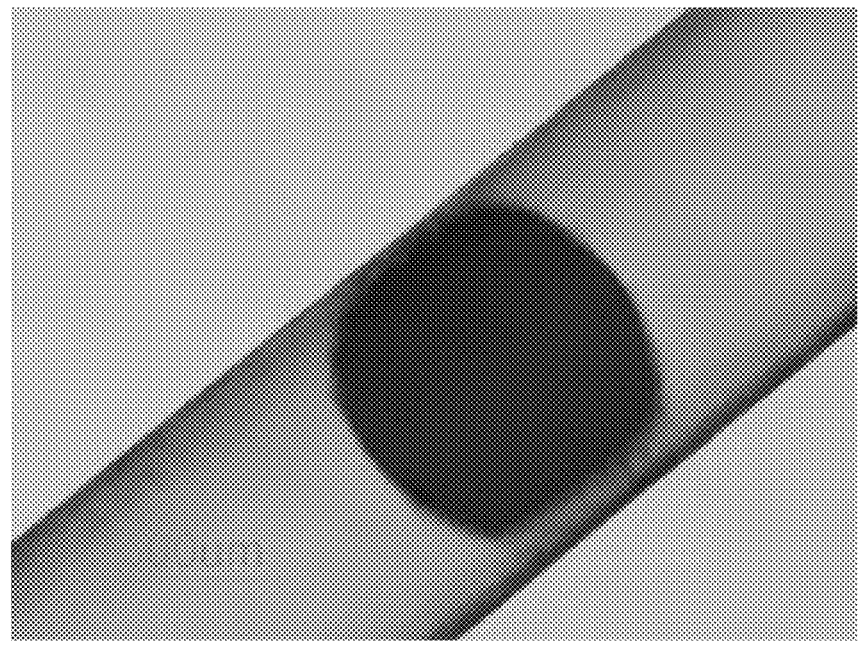

FIGS. 31A and 31B are light microscopy images of an example of microspheres loaded with doxorubicin while passing through a polyethylene tube. The microspheres illustrated in FIGS. 31A and 31B have a diameter between about 500 µm and about 700 µm. The catheter shown in FIGS. 31A and 31B had an internal diameter of about 580 µm (PE-50).

Figure 32A:
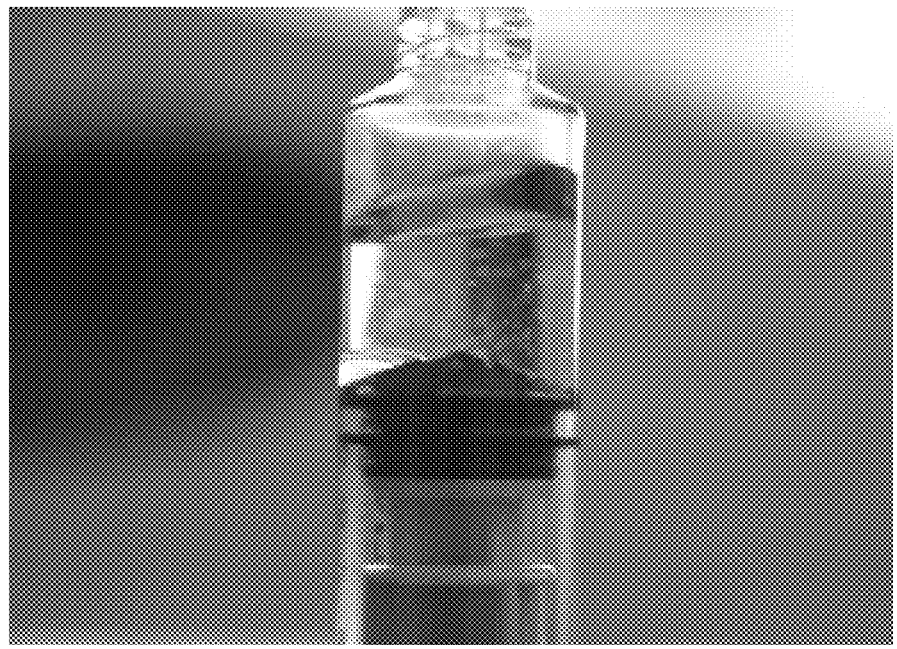
FIGS. 32A and 32B are images illustrating microspheres comprising CCN crosslinked with CMC suspended in two 4:6 contrast/saline mixtures.
Figure 32B:
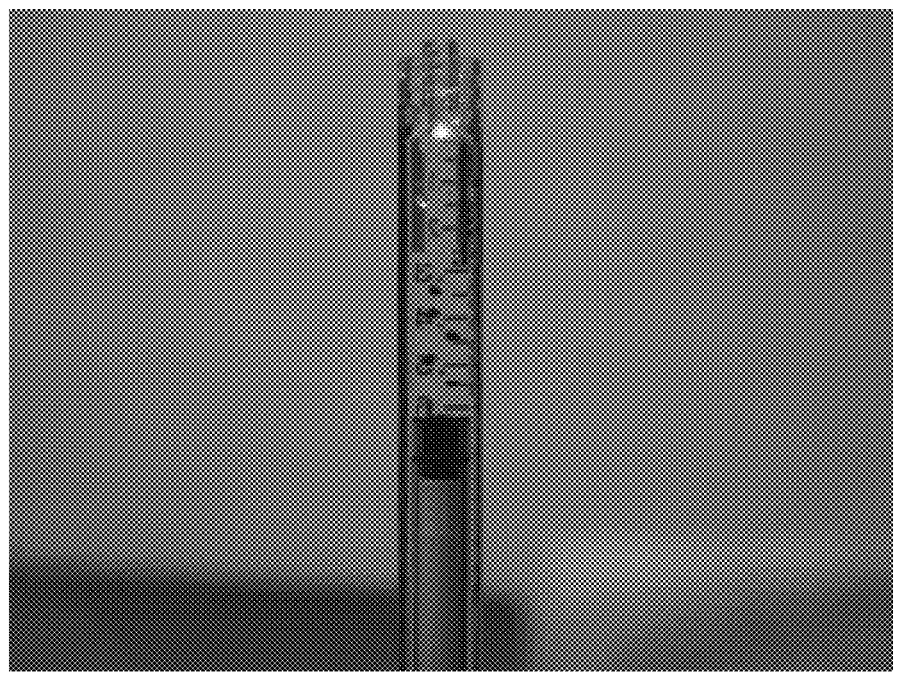

Microspheres according to the present invention may be suspended in a variety of solvents. For example, FIGS. 32A and 32B are images illustrating microspheres comprising CCN crosslinked with CMC suspended in two different mixtures. In FIG. 32A, the microspheres are suspended in a mixture of 40% contrast medium and 60% saline. As FIG. 32A illustrates, the microspheres are suspended in the mixture, and are translucent. FIG. 32B illustrates microspheres dyed with Evan's blue suspended in a 50% contrast medium and 50% saline mixture.

Figure 33:
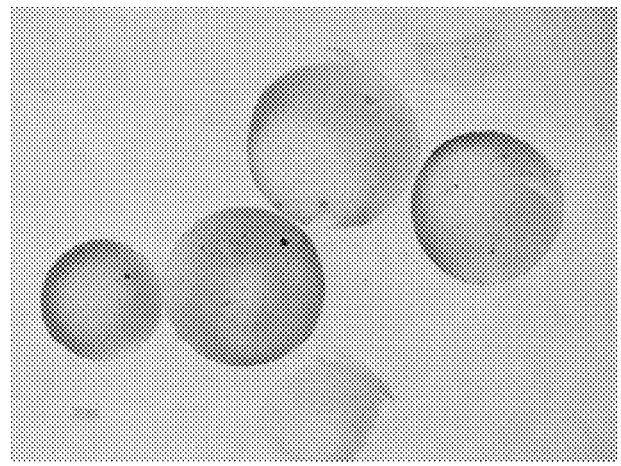
FIG. 33 is a light microscopy image of an example of a plurality of microspheres comprising CCN crosslinked with CMC after being stored for two months in water.

Microspheres comprising CNN crosslinked with CMC may be somewhat stable when stored in water, but eventually may begin to degrade. FIG. 33 is a light microscopy image of an example of a plurality of microspheres after being stored for two months in water. The microspheres shown in FIG. 33 had a crosslinking density of about 10%. The microspheres shown in FIG. 33 have been dyed with Evan's blue to increase contrast with the background medium (water). As FIG. 33 illustrates, the microspheres have begun to degrade and show decreased mechanical integrity.

Figure 34A:
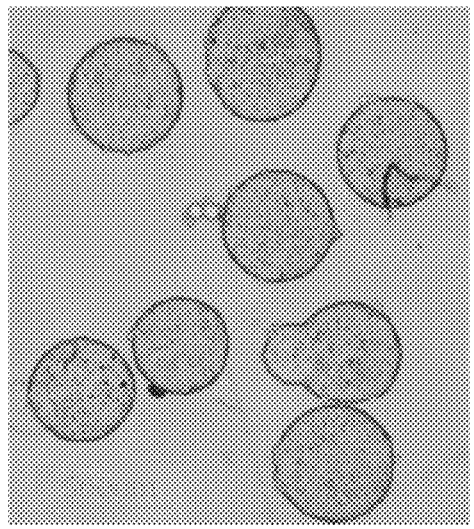
FIGS. 34A-34E are light microscopy images that illustrate an example of a plurality of microspheres comprising CCN crosslinked with CMC degrading in the presence of lysozyme.
Figure 34B:
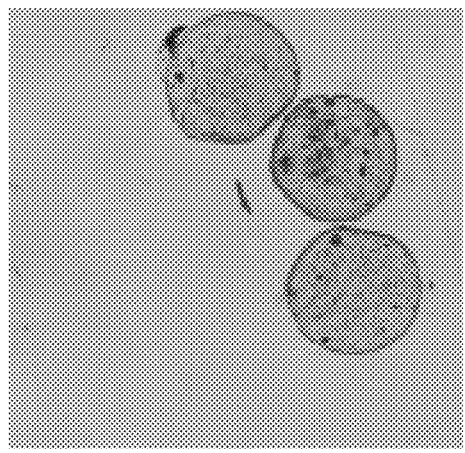
Figure 34C:
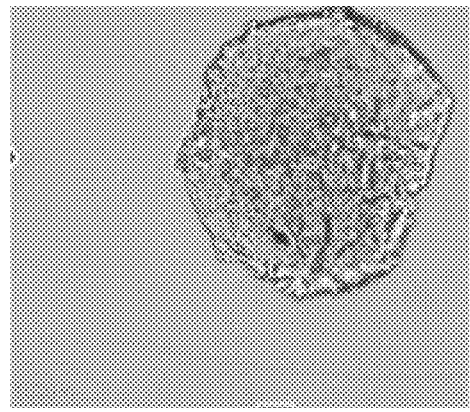
Figure 34D:
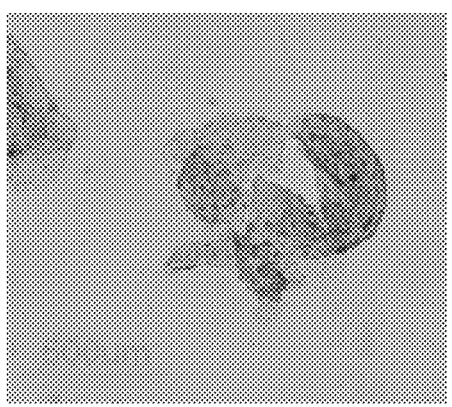
Figure 34E:
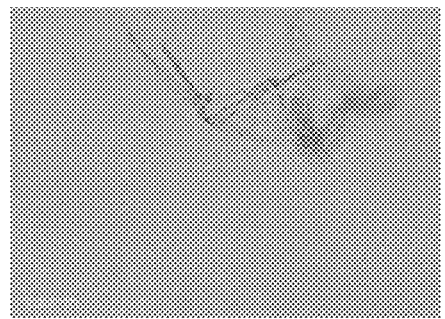

In some examples, microspheres comprising CCN crosslinked with CMC may degrade more rapidly in the presence of an enzyme such as lysozyme. FIGS. 34A-34E are light microscopy images that illustrate an example of a plurality of microspheres degrading in the presence of lysozyme. The microspheres had a crosslinking density of about 10%. The medium surrounding the microspheres contained 4 mg/mL lysozyme and the microspheres and surrounding medium were kept at a temperature of about 37° C. for the duration of the test. FIG. 34A illustrates the appearance of the microspheres on day 0, soon after the microspheres were placed in the medium. FIG. 34B shows the appearance of the microspheres on day 3. FIG. 34C illustrates the appearance of a microsphere after 7 days. Visual evidence of the beginning of degradation is apparent. FIG. 34D shows the appearance of a microsphere on day 9. Degradation of the microsphere is progressing, mechanical integrity is decreasing, and the microsphere is no longer spherical. Finally, FIG. 34E illustrates the appearance of a microsphere on day 14, at which time pieces of microsphere can be found in the medium, but the microsphere is no longer spherical.

As described above, the degradation time of the microspheres may be adjusted by increasing or decreasing the crosslink density in the microspheres. For example, a higher crosslink density, which may correspond to a higher oxidation degree of the partially oxidized CMC, may lead to an increased degradation time, while a lower crosslink density (a lower oxidation degree of the CMC) may lead to a decreased degradation time.

FIGS. 35A-35C are light microscopy images that illustrate another example of a plurality of microspheres loaded with doxorubicin degrading in the presence of lysozyme. The microspheres were prepared from OCMC-II (preparation described in Example 1 below) and CCN-III (preparation described in Example 6 below) and had diameters ranging from about 500 µm to about 700 µm. The microspheres were placed in a 2 mg/mL solution of doxorubicin in saline for about 24 hours to load the microspheres with doxorubicin. The medium surrounding the microspheres contained 4 mg/mL lysozyme in PBS and the microspheres and PBS were kept at a temperature of about 37° C. for the duration of the test. FIG. 35A illustrates the appearance of the microspheres on day 0, soon after the microspheres were placed in the PBS. FIG. 35B shows the appearance of the microspheres after about 1.5 months. FIG. 35C illustrates the appearance of a microsphere after about 3 months. Visual evidence of the beginning of degradation is apparent in FIG. 35C.

Figures 36A, 36B:
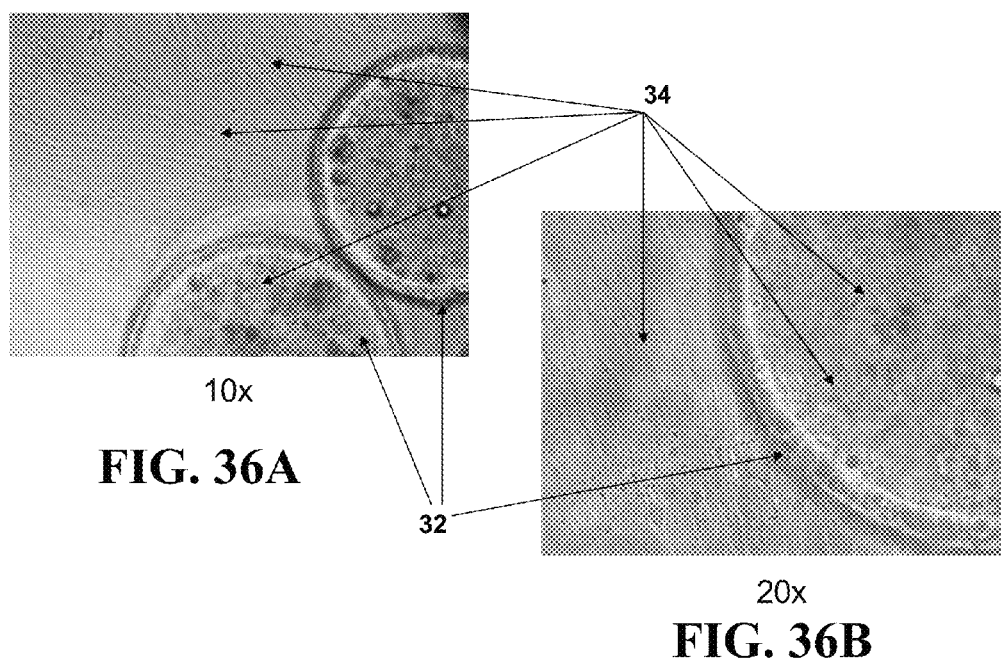
FIGS. 36A and 36B are light microscopy images illustrating an example of human dermal fibroblasts cultured with microspheres comprising CCN crosslinked with CMC according to an aspect of the disclosure.

FIGS. 36A and 36B are light microscopy images illustrating an example of microspheres comprising CCN crosslinked with CMC 32 cultured with human dermal fibroblasts 34. The human dermal fibroblasts 34 show no apparent adverse effects due to the presence of microspheres 32.

Figure 37A:
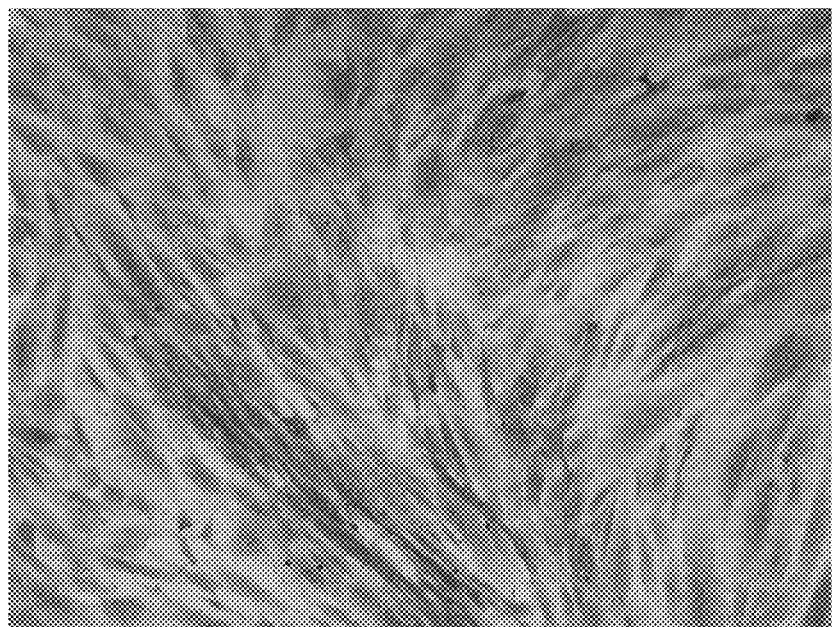
FIGS. 37A and 37B are light microscopy images of an example control including cultured human fibroblast and an example of a sample including human fibroblast cultured with microspheres comprising CCN crosslinked with CMC according to an aspect of the disclosure.
Figure 37B:
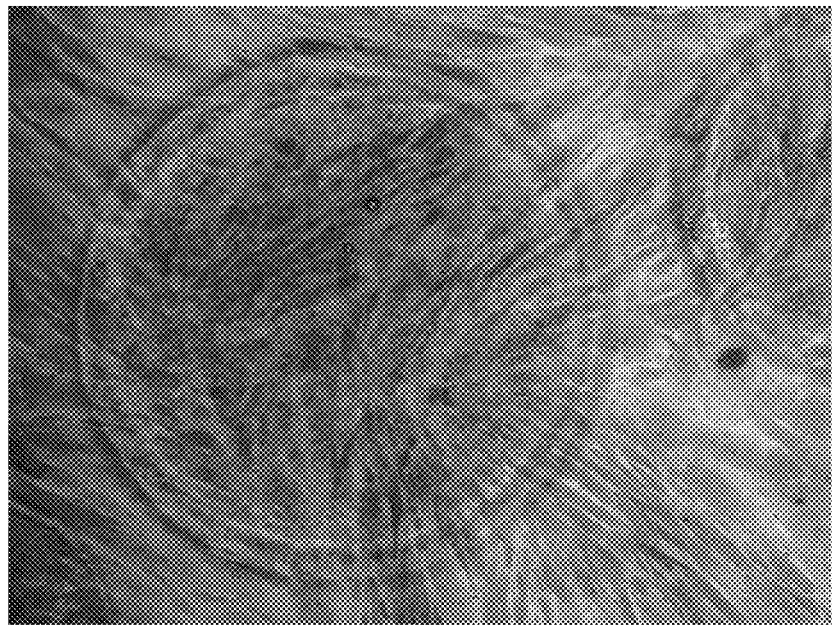

FIGS. 37A and 37B are light microscopy images of an example control including cultured human fibroblast and an example of a sample including human dermal fibroblast cultured with microspheres comprising CCN crosslinked with CMC, respectively. The control and sample have been stained with crystal violet. Again, the human dermal fibroblast shows no apparent adverse effects due to the presence of microspheres.

Figure 38A:
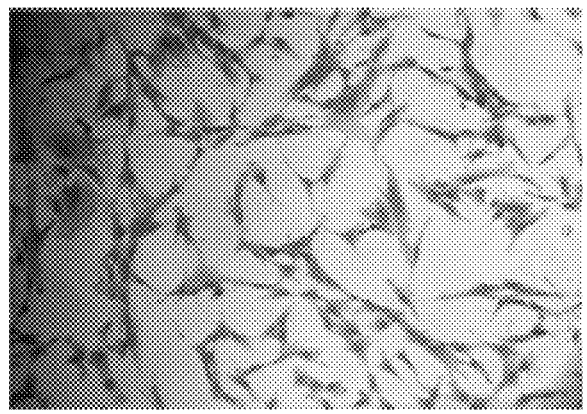
FIG. 38A-38C are light microscopy images illustrating an example of human dermal fibroblasts stained with crystal violet.
Figure 38B:
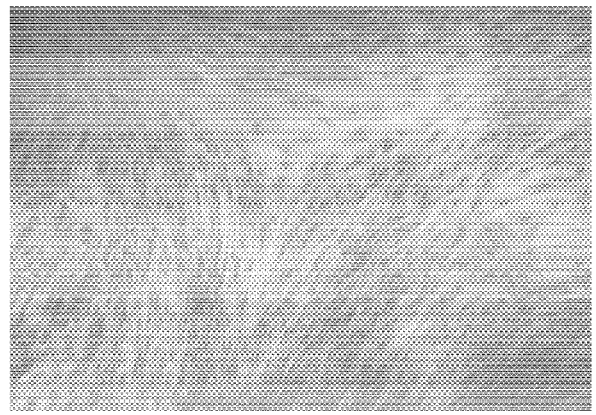
Figure 38C:
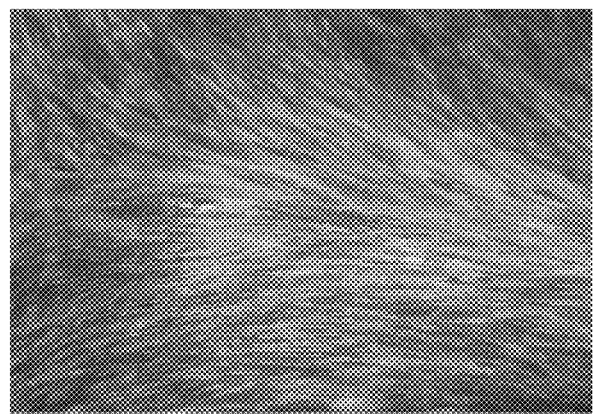

FIG. 38A-38C are light microscopy images illustrating an example of a control that included human dermal fibroblasts stained with crystal violet. FIG. 38A is an image collected about 3 days after beginning of the fibroblast culture. FIG. 38B is an image collected about 7 days after beginning of the fibroblast culture. FIG. 38C is an image collected about 15 days after beginning of the fibroblast culture.

Figure 39A:
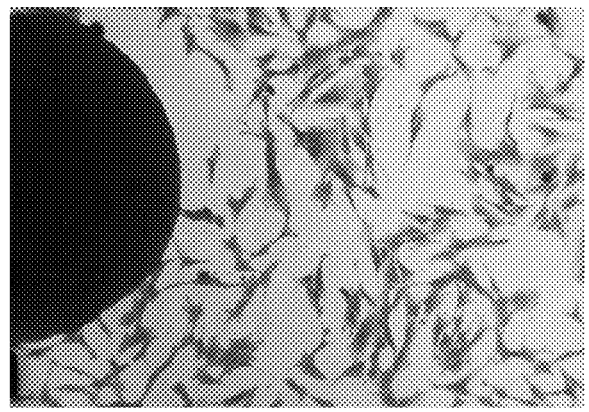
FIG. 39A-39C are light microscopy images illustrating an example of a sample including human dermal fibroblast cultured with microspheres comprising CCN crosslinked with CMC according to an aspect of the disclosure.
Figure 39B:
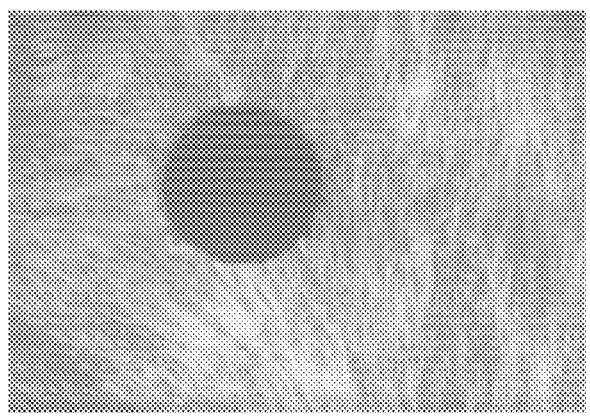
Figure 39C:
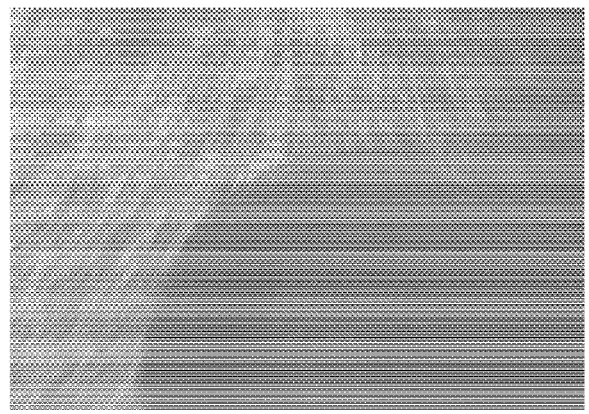

FIGS. 39A-39C are light microscopy images illustrating an example of a sample including human dermal fibroblast cultured with microspheres comprising CCN crosslinked with CMC. The microspheres were prepared from OCMC-I (preparation described in Example 1 below) and CCN-II (preparation described in Example 5 below). The cells were stained with crystal violet. FIG. 39A is an image collected about 3 days after beginning of the culture. FIG. 39B is an image collected about 7 days after beginning of the culture. FIG. 39C is an image collected about 15 days after beginning of the culture. Compared with the control shown in FIGS. 38A-38C, the human dermal fibroblast in FIGS. 39A-39C shows no apparent adverse effects due to the presence of microspheres.

Figure 40:
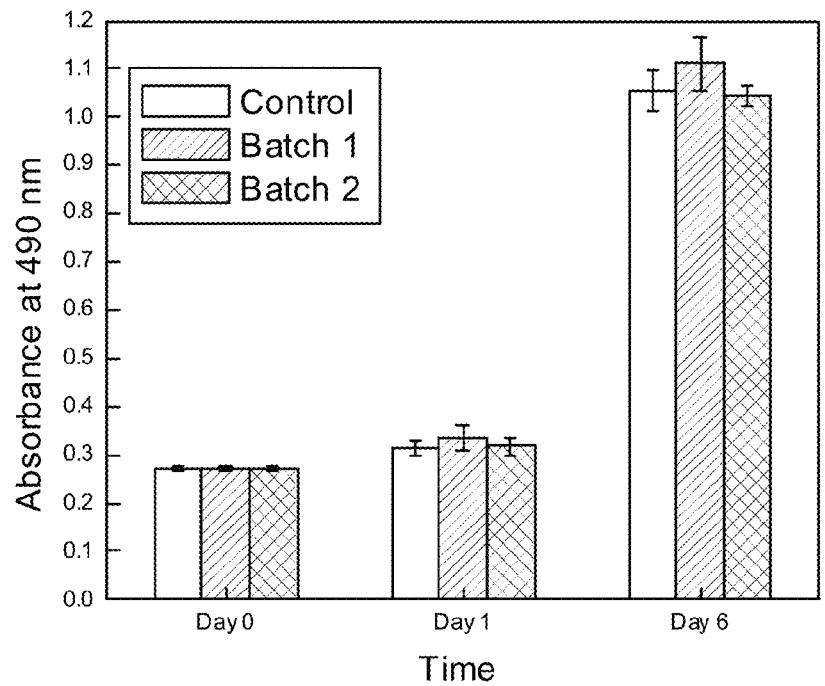
FIG. 40 is a bar graph that illustrates an example of absorbance at a wavelength of about 490 nm of medium cultured with human dermal fibroblasts after being treated with MTS

FIG. 40 is a bar graph that illustrates an example of absorbance at a wavelength of about 490 nm of medium cultured with human dermal fibroblasts after being treated with MTS (3-(4,5-dimethylthiazol-2-yl)-5-(3-carboxymethoxyphenyl)-2-(4-sulfophenyl)-2H-tetrazolium, inner salt). MTS is a cell titer for live cells, and thus the absorbance is proportional to the number of live cells in the culture. The control included only human dermal fibroblast, while batch 1 and batch 2 included human dermal fibroblast cultured with microspheres formed of CCN crosslinked with CMC. Microspheres in batch 1 were prepared from OCMC-I (preparation described in Example 1 below) and CCN-I (preparation described in Example 4 below). Microspheres in batch 2 were prepared from OCMC-II and CCN-I (preparation described in Example 5 below). FIG. 40 shows that in this example, there was no significant difference in cell growth over the course of six days between the control, batch 1, and batch 2.

Figure 41:
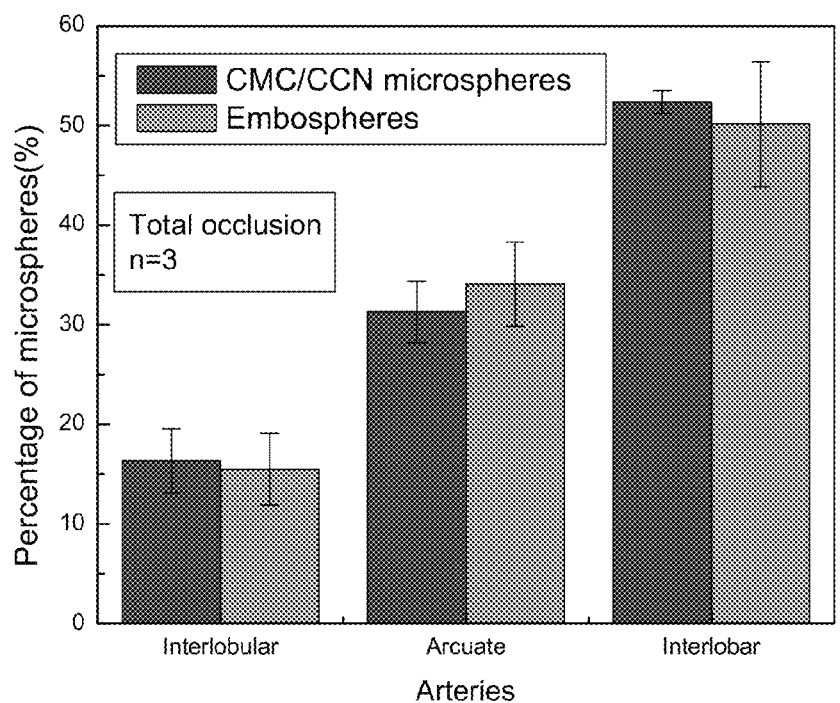
FIG. 41 is a bar graph that illustrates an example of the arterial distribution of the microspheres after embolization of three pairs of rabbit kidneys with microspheres having diameters between about 100 μm and about 300 μm.

FIG. 41 is a bar graph that illustrates an example of the arterial distribution of the microspheres after embolization of three pairs of rabbit kidneys with microspheres having diameters between about 100 μm and about 300 μm. For comparative purposes, microspheres available under the trade designation Embosphere® (available from BioSphere Medical, Inc., Rockland, Mass., U.S.A.) having diameters between about 100 μm and about 300 μm were used. In each example, microspheres were injected into the renal artery of live rabbits. The rabbits were then euthanized and the kidneys removed to assess the results of the embolization. The numbers of microspheres for each of the Embosphere® microspheres and the microspheres formed of CCN crosslinked with CMC were counted at a first location in the interlobar artery (proximal to the injection site), the arcuate artery (median), and at a second location in the interlobar artery (distal to the injection site). The results are shown in FIG. 41 as a percentage of the microspheres counted at each location.

Figure 42:
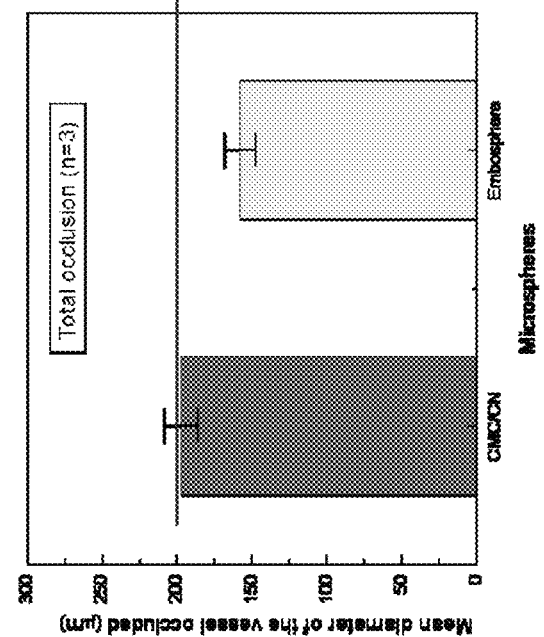
FIG. 42 is bar diagram that illustrates an example comparison between Embospheres® and microspheres formed of CCN crosslinked with CMC of the mean diameter of the vessel occluded during an embolization procedure.

FIG. 42 is bar diagram that illustrates an example comparison between Embospheres® and microspheres formed of CCN crosslinked with CMC of the mean diameter of the vessel occluded during an embolization procedure. In some examples, it may be desirable that the microspheres occlude arteries with a certain, predetermined diameter. Accordingly, it may be desirable to understand the relationship between a size range of the microspheres and the average diameter occluded by the microspheres. As in FIG. 41, the nominal diameter of the Embospheres® used in the example shown in FIG. 42 was between 100 μm and 300 μm. Similarly, the nominal diameter of the microspheres formed of CCN crosslinked with CMC was between 100 μm and 300 μm. The mean diameter occluded by the Embospheres® was about 150 μm, while the mean diameter occluded by the microspheres formed of CCN crosslinked with CMC was about 200 μm.

Figure 43:
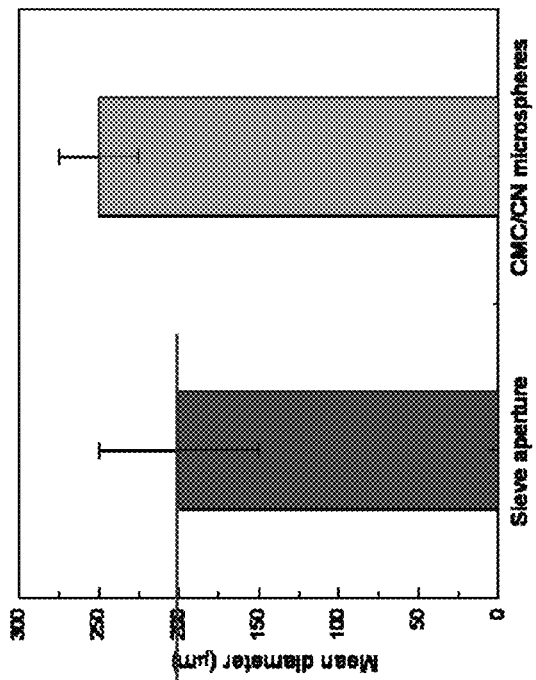
FIG. 43 is a bar diagram that illustrates an example determination of the mean diameter of the microspheres formed of CCN crosslinked with CMC that were used in the embolization procedure that generated the results shown in FIG. 43.

FIG. 43 is a bar diagram that illustrates an example determination of the mean diameter of the microspheres formed of CCN crosslinked with CMC that were used in the embolization procedure that generated the results shown in FIG. 42. The bar labeled "CMC/CN microspheres" shows the mean diameter of the microspheres formed of CCN crosslinked with CMC as determined by optical micrography. The bar labeled "Sieve aperture" shows the calibrated mean diameter of the microspheres formed of CCN crosslinked with CMC, determined by passing sieves with different apertures and averaging the aperture sizes of the two adjacent sieves aperture, one of which the microspheres did not pass through and one of which the microspheres did pass through. In this way, the sieve aperture mean diameter may be considered the mean diameter of compressed microspheres formed of CCN crosslinked with CMC. As shown in FIGS. 42 and 43, the sieve aperture mean diameter is substantially the same as the mean diameter of the vessel occluded by the microspheres formed of CCN crosslinked with CMC. This suggests that determining a sieve aperture mean diameter for microspheres formed of CCN crosslinked with CMC may predict a mean diameter of a vessel that may be occluded by the microspheres.

Figure 44:
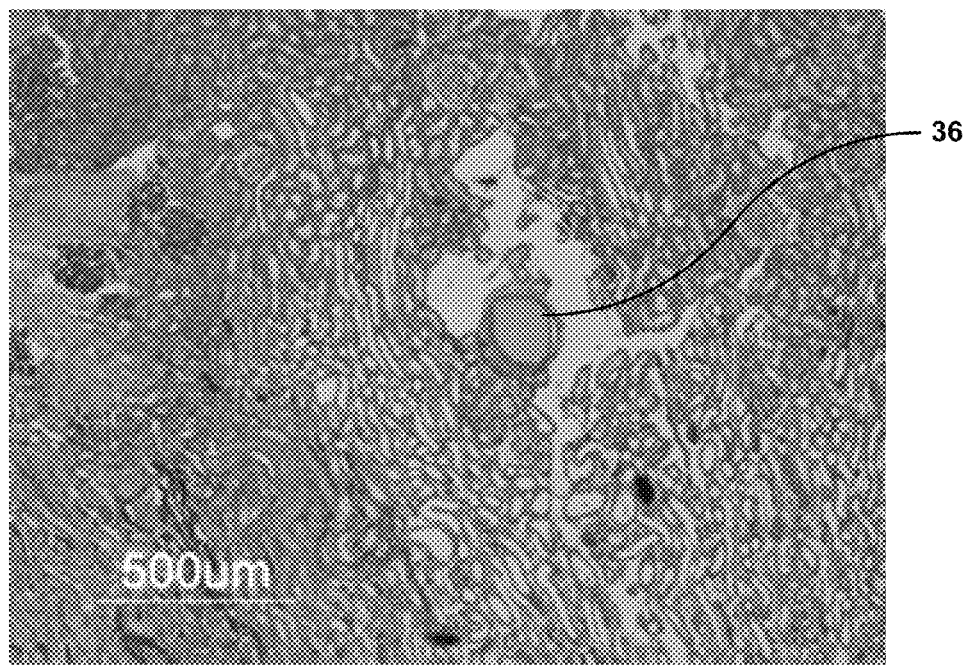
FIGS. 44 and 45 are example histology sections of kidney tissue showing arcuate artery in a kidney of a rabbit occluded with an embolic microsphere according to aspects of the disclosure.
Figure 45:
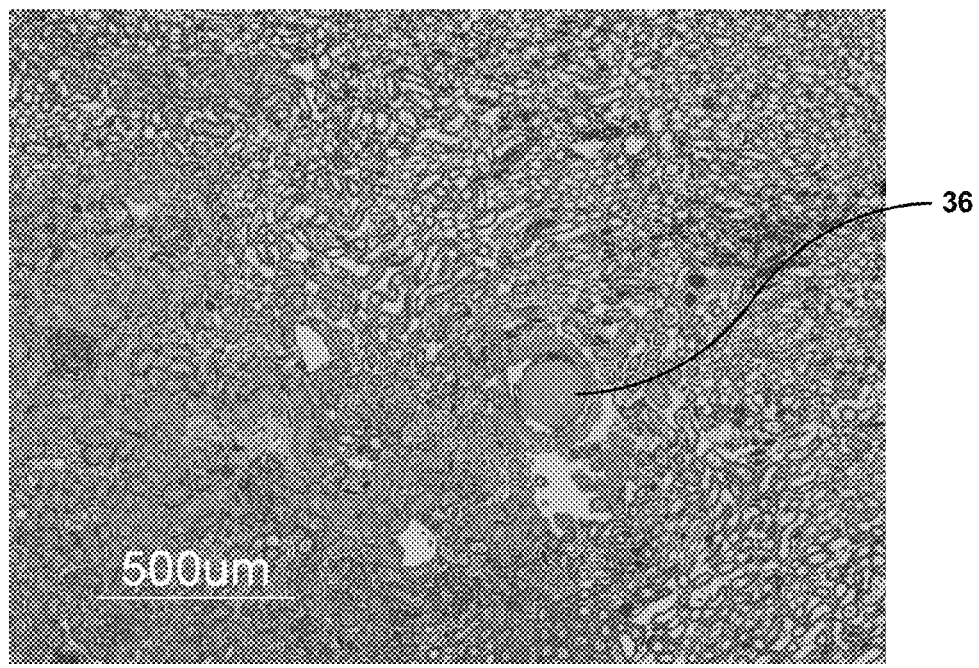

FIGS. 44 and 45 are example histology sections of kidney tissue showing arcuate artery in a kidney of a rabbit occluded with an embolic microsphere 36 according to aspects of the disclosure. As shown in FIGS. 44 and 45, the embolic microsphere 36 occludes substantially all of the artery. The small interval between the embolic microsphere 36 and the wall of the vessel is believed to be caused by sample processing as the microsphere 36 shrinks upon fixation.

Microspheres formed according to the present disclosure may be utilized for a number of applications. For example, one application for an embolic microsphere comprising CCN crosslinked by CMC is transareterial chemoembolization (TACE) of liver tumors. TACE for unresectable hepatocellular carcinoma (HCC) is an approved treatment modality that increases patient survival compared to intravenous chemotherapy. TACE includes intraarterial (via the hepatic artery) injection of chemotherapeutic agents followed by embolization of tumoral feeding arteries. The trend in TACE is to use drug eluting beads loaded with chemotherapeutic agents that are progressively released into the tumor. Drug eluting TACE is associated with less systemic toxicity and a better patient tolerance. Because the microsphere comprising CCN crosslinked by CMC is bioresorbable and is thus absorbed by the body of the patient over time after injection, the release profile of the chemotherapeutic agents may be controlled. Additionally, the microsphere comprising CCN crosslinked by CMC may act as combination chemotherapeutic agent carriers and embolization agents. Furthermore, because the microsphere comprising CCN crosslinked by CMC are bioresorbable, artery integrity may be restored upon resorption, which may be advantageous in some examples.

Another application for microspheres comprising CCN crosslinked by CMC is Uterine Fibroids Embolization (UFE). Uterine Fibroids are benign muscular tumors that grow in the wall of the uterus. Uterine fibroids can grow as a single tumor or as many tumors. Uterine fibroids can be either as small as an apple seed or as big as a grapefruit. In unusual cases uterine fibroids can become very large. An increasingly accepted therapy technique for uterine fibroids is UFE. The main purpose of UFE is to reduce the size of the fibroid and to treat excessive uterine bleeding. In essence, UFE involves the placement of a catheter into the uterine arteries and injection of embolization microspheres into the uterine arteries to achieve fibroid devascularzation and progressive shrinkage. Use of bioresorbable microspheres comprising CCN crosslinked by CMC may facilitate restoration of uterine artery integrity after embolization.

EXAMPLES

Example 1

Preparation of Partially Oxidized CMC

About 1 g of sodium carboxymethyl cellulose (Sigma-Aldrich, St. Louis, Mo., $M_w$ about 700,000 g/mol) and 80 mL distilled water were added to a 250 mL flask. After the carboxymethyl cellulose dissolved substantially completely, 25% molar equivalent of sodium periodate in 20 mL distilled water was added to the flask. The reaction was allowed to proceed for 24 hours at about 25° C. After 24 hours, about 0.21 g ethylene glycol was added to the flask to stop the reaction. After an additional 30 minutes, the mixture was poured into a dialysis tube (MWCO 3500) to dialyze against distilled water for 3 days. Dry product was obtained by lyophilizing the dialyzed solution. The resulting partially oxidized CMC was labeled OCMC-II.

Example 2

Preparation of Partially Oxidized CMC

About 1 g of sodium carboxymethyl cellulose (Sigma-Aldrich, St. Louis, Mo., $M_w$ about 700,000 g/mol) and 80 mL distilled water were added to a 250 mL flask. After the carboxymethyl cellulose dissolved substantially completely, 10% molar equivalent of sodium periodate in 20 mL distilled water was added to the flask. The reaction was allowed to proceed for 24 hours at about 25° C. After 24 hours, about 0.08 g ethylene glycol was added to the flask to stop the reaction. After an additional 30 minutes, the mixture was poured into a dialysis tube (MWCO 3500) to dialyze against distilled water for 3 days. Dry product was obtained by lyophilizing the dialyzed solution. The resulting partially oxidized CMC was labeled OCMC-I.

Example 3

Preparation of Partially Oxidized CMC

About 1 g of sodium carboxymethyl cellulose (Sigma-Aldrich, St. Louis, Mo., $M_w$ about 700,000 g/mol) and 80 mL distilled water were added to a 250 mL flask. After the carboxymethyl cellulose dissolved substantially completely, 50% molar equivalent of sodium periodate in 20 mL distilled water was added to the flask. The reaction was allowed to proceed for 24 hours at about 25° C. After 24 hours, about 0.42 g ethylene glycol was added to the flask to stop the reaction. After an additional 30 minutes, the mixture was poured into a dialysis tube (MWCO 3500) to dialyze against distilled water for 3 days. Dry product was obtained by lyophilizing the dialyzed solution. The resulting partially oxidized CMC was labeled OCMC-III.

Example 4

Preparation of CCN

In a 3-neck flask, about 2 g chitosan (Sigma-Aldrich, St. Louis, Mo., greater than 75% deacetylated) was added to a mixture of about 16 g sodium hydroxide, about 20 mL distilled water, and about 20 mL isopropanol. The mixture was stirred at about 25° C. for about 24 hours. Before carboxymethylation, the flask was maintained in a water bath at about 50° C. for about 1 hour. About 16 g monochloroacetic acid (Sigma-Aldrich, St. Louis, Mo.) in 10 mL isopropanol then was added dropwise into the reaction mixture. The reaction mixture was stirred at about 50° C. for an additional 4 hrs, and the reaction was stopped by adding about 80 mL of 70% ethanol. The precipitate was filtered and rinsed thoroughly with 70-90% ethanol and vacuum dried at room temperature.

The dried product was dissolved in about 100 mL water and homogenized for 2 hours. Any insoluble residue present in the mixture was removed by centrifuging. The supernatant was dialyzed in an MWCO 3500 dialysis tube against distilled water and then lyophilized. The resulting CCN was labeled CCN-I.

Example 5

Preparation of CCN

In a 3-neck flask, about 2 g chitosan (Sigma-Aldrich, St. Louis, Mo., greater than 75% deacetylated) was added to a mixture of about 8 g sodium hydroxide, about 10 mL distilled water, and about 10 mL isopropanol. The mixture was stirred at room temperature for about 24 hours. Before carboxymethylation, the flask was maintained in a water bath at about 50° C. for about 1 hour. About 8 g monochloroacetic acid (Sigma-Aldrich, St. Louis, Mo.) in 5 mL isopropanol then was added dropwise into the reaction mixture. The reaction mixture was stirred at about 50° C. for an additional 4 hrs, and the reaction was stopped by adding about 80 mL of 70% ethanol. The precipitate was filtered and rinsed thoroughly with 70-90% ethanol and vacuum dried at room temperature.

The dried product was dissolved in about 100 mL water and homogenized for 2 hours. Any insoluble residue present in the mixture was removed by centrifuging. The supernatant was dialyzed in an MWCO 3500 dialysis tube against distilled water and then lyophilized. The resulting CCN was labeled CCN-II.

Example 6

Preparation of CCN

In a 3-neck flask, about 2 g chitosan (Sigma-Aldrich, St. Louis, Mo., greater than 75% deacetylated) was added to a mixture of about 8 g sodium hydroxide, about 8 mL distilled water, and about 32 mL isopropanol. The mixture was stirred for about 24 hours at about 25° C. Before carboxymethylation, the flask was maintained in a water bath at about 50° C. for about 1 hour. About 16 g monochloroacetic acid (Sigma-Aldrich, St. Louis, Mo.) in 10 mL isopropanol then was added dropwise into the reaction mixture. The reaction mixture was stirred at about 50° C. for an additional 4 hrs, and the reaction was stopped by adding about 80 mL of 70% ethanol. The precipitate was filtered and rinsed thoroughly with 70-90% ethanol and vacuum dried at room temperature.

The dried product was dissolved in about 100 mL water and homogenized for 2 hours. Any insoluble residue present in the mixture was removed by centrifuging. The supernatant was dialyzed in an MWCO 3500 dialysis tube against distilled water and then lyophilized. The resulting CCN was labeled CCN-III.

Example 7

Preparation of CCN and CMC Microspheres

About 0.075 g of CCN-I was mixed in about 5 mL of water to form a 1.5% w/v CCN-I solution. Similarly, about 0.075 g OCMC-I was mixed in about 5 ml water to form a 1.5% w/v OCMC-I solution. The CCN-I and OCMC-I solutions were then mixed. The mixture was added to about 50 mL mineral oil containing between 0.2 mL and 0.5 mL sorbitane monooleate to form an emulsion. The emulsion was homogenized for about 45 minutes. The aqueous phase of the emulsion was allowed to evaporate over night at about 45° C. with constant stirring. The crosslinked CCN and CMC was isolated by precipitation in isopropanol followed by centrifugation to remove the oil phase. The resulting microspheres were washed thoroughly in acetone before being dried under vacuum. The mean diameter of the microspheres, measured in normal saline by a light microscope, was about 515±3 μm.

Example 8

Preparation of CCN and CMC Microspheres

About 0.075 g of CCN-I was mixed in about 5 mL of water to form a 1.5% w/v CCN-I solution. Similarly, about 0.075 g OCMC-II was mixed in about 5 ml water to form a 1.5% w/v OCMC-I solution. The CCN-I and OCMC-II solutions were then mixed. The mixture was added to about 50 mL mineral oil containing between 0.2 mL and 0.5 mL sorbitane monooleate to form an emulsion. The emulsion was homogenized for about 45 minutes. The aqueous phase of the emulsion was allowed to evaporate over night at about 45° C. with constant stirring. The crosslinked CCN and CMC was isolated by precipitation in isopropanol followed by centrifugation to remove the oil phase. The resulting microspheres were washed thoroughly in acetone before being dried under vacuum. The mean diameter of the microspheres, measured in normal saline by a light microscope, was about 594±3 μm.

Example 9

Preparation of CCN and CMC Microspheres

About 0.075 g of CCN-I was mixed in about 5 mL of water to form a 1.5% w/v CCN-I solution. Similarly, about 0.075 g OCMC-III was mixed in about 5 ml water to form a 1.5% w/v OCMC-I solution. The CCN-I and OCMC-III solutions were then mixed. The mixture was added to about 50 mL mineral oil containing between 0.2 mL and 0.5 mL sorbitane monooleate to form an emulsion. The emulsion was homogenized for about 45 minutes. The aqueous phase of the emulsion was allowed to evaporate over night at about 45° C. with constant stirring. The crosslinked CCN and CMC was isolated by precipitation in isopropanol followed by centrifugation to remove the oil phase. The resulting microspheres were washed throrougly in acetone before being dried under vacuum. The mean diameter of the microspheres, measured in normal saline by a light microscope was about 702±3 μm.

Example 10

Preparation of CCN and CMC Microspheres

About 0.1 g of CCN-II was mixed in about 5 mL of water to form a 2% w/v CCN-I solution. Similarly, about 0.1 g OCMC-II or 0.1 OCMC-III was mixed in about 5 ml water to form a 2% w/v OCMC-II solution or a 2% w/v OCMC-III solution. The CCN-I and OCMC-I solutions were then mixed. The mixture was added to about 50 mL mineral oil containing between 0.2 mL and 0.5 mL sorbitane monooleate to form an emulsion. The emulsion was homogenized for about 45 minutes. The aqueous phase of the emulsion was allowed to evaporate over night at about 45° C. with constant stirring. The crosslinked CCN and CMC was isolated by precipitation in isopropanol followed by centrifugation to remove the oil phase. The resulting microspheres were washed thoroughly in acetone before being dried under vacuum. The mean diameter of the microspheres, measured in normal saline by a light microscope was about 2000 μm.

Example 11

Preparation of Doxorubicin-loaded Microspheres

Microspheres disposed in saline and having wet weight of about 150 mg were added into a 22 mL glass vial. (The microspheres had a dry weight of about 17 mg and were formed from OCMC-II and CCN-III.) Excess saline was removed with a pipette. About 20 mL doxorubicin solution (about 2 mg doxorubicin/mL solution) was formed by dissolving doxorubicin in a saline/hydrochloric acid solution having a pH between about 2.5 and about 4.5 and was added into the vial. An amount of doxorubicin remaining in the loading solution after loading of the microspheres was determined by measuring the absorbance at 482 nm using a Beckman UV-Visible spectrophotometer and comparison to a standard curve constructed from solutions of known concentrations of drug. The maximum loading is between about 0.3 and about 0.7 mg doxorubicin per mg dry microspheres, depending on the size of the microspheres.

Example 12

Release of Doxorubicin in Saline

About 3 mg of loaded microspheres and about 2 mL normal saline were added into a disposable plastic cuvette. The concentration of doxorubicin released in the medium was monitored with a Beckman UV-Visible spectrophotometer. The release of the doxorubicin was accomplished both with replacing normal saline at periodic intervals (on day 1, day 3, day 6, day 12, day 19, and day 26) and without replacing the normal saline. The saline was saturated with doxorubicin in about 2 weeks when the normal saline was not replaced. The release of doxorubicin when replacing the normal saline can last 1 month without saturating the normal saline.

Various embodiments of the disclosure have been described. These and other embodiments are within the scope of the following claims.

The invention claimed is:

1. A material comprising at least one microsphere comprising carboxymethyl chitosan crosslinked with carboxymethyl cellulose, wherein the at least one microsphere comprises a crosslinking density between the carboxymethyl chitosan and the carboxymethyl cellulose that results in a fracture strain of the at least one microsphere between about 70% and about 90%.

2. The material of claim 1, wherein the at least one microsphere comprises a diameter between about 100 micrometers and about 1200 micrometers.

3. The material of claim 1, wherein the at least one microsphere comprises a diameter of between about 300 micrometers and about 500 micrometers.

4. The material of claim 1, wherein the at least one microsphere comprises a diameter of between about 100 micrometers and about 300 micrometers.

5. The material of claim 1, wherein the at least one microsphere comprises a diameter of between about 700 micrometers and about 900 micrometers.

6. The material of claim 1, wherein the at least one microsphere comprises a diameter of between about 900 micrometers and about 1200 micrometers.

7. The material of claim 1, wherein the at least one microsphere further comprises a therapeutic agent.

8. The material of claim 7, wherein the therapeutic agent comprises a chemotherapeutic agent.

9. The material of claim 7, wherein the therapeutic agent comprises at least one positively charged functional group.

10. The material of claim 7, wherein the therapeutic agent comprises at least one of irinotecan, ambroxol, or doxorubicin.

11. The material of claim 7, wherein a concentration of the therapeutic agent is between about 0.3 milligram of therapeutic agent per milligram of dry microsphere and 0.75 milligram of therapeutic agent per milligram of dry microsphere.

12. The material of claim 1, wherein the microsphere is substantially free of a small molecule crosslinking agent.

13. An suspension comprising:
  a solvent; and
  a plurality of microspheres suspended in the solvent, wherein at least one microsphere of the plurality of microspheres comprises carboxymethyl chitosan crosslinked with carboxymethyl cellulose, and wherein the at least one microsphere comprises a crosslinking density between the carboxymethyl chitosan and the carboxymethyl cellulose that results in a fracture strain of the at least one microsphere between about 70% and about 90%.

14. The suspension of claim 13, wherein the solvent comprises a mixture of contrast medium and saline.

15. The suspension of claim 14, wherein the mixture comprises between about 40 vol. % contrast medium and about 60 vol. % saline, and about 50 vol. % contrast medium and about 50 vol. % saline.

16. The suspension of claim 13, wherein the at least one microsphere comprises a diameter between about 100 micrometers and about 1200 micrometers.

17. The suspension of claim 13, wherein the at least one microsphere comprises a diameter of between about 300 micrometers and about 500 micrometers.

18. The suspension of claim 13, wherein the at least one microsphere comprises a diameter of between about 100 micrometers and about 300 micrometers.

19. The suspension of claim 13, wherein the at least one microsphere comprises a diameter of between about 700 micrometers and about 900 micrometers.

20. The suspension of claim 13, wherein the at least one microsphere comprises a diameter of between about 900 micrometers and about 1200 micrometers.

21. The suspension of claim 13, wherein the at least one microsphere further comprises a therapeutic agent.

22. The suspension of claim 21, wherein the therapeutic agent comprises a chemotherapeutic agent.

23. The suspension of claim 21, wherein the therapeutic agent comprises at least one positively charged functional group.

24. The suspension of claim 21, wherein the therapeutic agent comprises at least one of irinotecan, ambroxol, or doxorubicin.

25. The suspension of claim 21, wherein a concentration of the therapeutic agent is between about 0.3 milligram of therapeutic agent per milligram of dry microsphere and about 0.75 milligram of therapeutic agent per milligram of dry microsphere.

26. The suspension of claim 13, wherein the at least one microsphere is substantially free of a small molecule crosslinking agent.

27. A method of forming a microsphere, the method comprising:
  at least partially oxidizing carboxymethyl cellulose (CMC) to form partially oxidized CMC, wherein the CMC comprises a weight average molecular weight of between about 50,000 grams per mole (g/mol) and about 800,000 g/mol prior to oxidation;
  forming an emulsion of partially oxidized CMC, carboxymethyl chitosan (CCN), water, and an oil, wherein the CCN comprises a weight average molecular weight of between about 190,000 g/mol and about 375,000 g/mol; and
  mixing the emulsion at a temperature of between about 20° C. and 70° C. for at least about 12 hours to crosslink the CCN with the CMC and form the microsphere, wherein the microsphere comprises a crosslinking density between the carboxymethyl chitosan and the carboxymethyl cellulose that results in a fracture strain of the microsphere between about 70% and about 90%.

28. The method of claim 27, wherein crosslinking the CCN with the CMC to form the embolic microsphere comprises mixing the emulsion at a temperature of about 50° C. for at least about 12 hours.

29. The method of claim 27, wherein at least partially oxidizing CMC to form partially oxidized CMC comprises at least partially oxidizing CMC to form partially oxidized CMC using $NaIO_4$.

30. The method of claim 29, wherein a molar ratio of $NaIO_4$ to CMC at the beginning of the oxidation reaction is between about 0.1:1 and about 0.5:1.

31. The method of claim 27, further comprising:
  mixing the partially oxidized CMC in a solvent at a concentration of between about 0.005 mg CMC per 1 mL water and about 0.03 mg CMC per 1 mL water to form a first solution; and
  mixing the CCN in a solvent at a concentration of between about 0.005 mg CCN per 1 mL water and about 0.03 mg CCN per 1 mL water to form a second solution, and
  wherein forming the emulsion of partially oxidized CMC, CCN, water, and the oil comprising mixing the first solution, the second solution, and the oil to form the emulsion of partially oxidized CMC, CCN, water, and the oil.

32. The method of claim 27, wherein the emulsion is substantially free of any small-molecule crosslinking agent.

* * * * *